United States Patent
Dorsch et al.

(10) Patent No.: US 6,492,368 B1
(45) Date of Patent: Dec. 10, 2002

(54) BENZAMIDINE DERIVATIVES AS FACTOR XA INHIBITORS

(75) Inventors: Dieter Dorsch, Ober-Ramstadt (DE); Hanns Wurziger, Darmstadt (DE); Guido Melzer, Hofheim/Ts. (DE); Horst Juraszyk, Seeheim (DE); Sabine Bernotat-Danielowski, Bad-Naumheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/509,729

(22) PCT Filed: Sep. 16, 1998

(86) PCT No.: PCT/EP98/05898

§ 371 (c)(1),
(2), (4) Date: Mar. 31, 2000

(87) PCT Pub. No.: WO99/16751

PCT Pub. Date: Apr. 8, 1999

(30) Foreign Application Priority Data

Oct. 1, 1997 (DE) .......................................... 197 43 435

(51) Int. Cl.$^7$ .................... A61K 31/495; A61K 31/496; C07D 295/192; C07D 295/26; C07D 413/12

(52) U.S. Cl. ........................... 514/252.12; 514/252.13; 514/254.03; 514/253.06; 514/254.04; 514/254.05; 514/253.13; 514/254.11; 514/255.01; 514/255.03; 544/363; 544/365; 544/367; 544/371; 544/375; 544/376; 544/377; 544/379; 544/383; 544/386; 544/387; 544/388; 544/392

(58) Field of Search ................................ 544/383, 363, 544/365, 367, 371, 375, 376, 377, 379, 386–388, 392; 514/255.01, 255.03, 252.13, 252.12, 253.13, 254.03, 254.11, 254.04, 254.05, 253.06

(56) References Cited

U.S. PATENT DOCUMENTS

| 5,442,064 | A | * | 8/1995 | Pieper et al. | ................. 544/360 |
| 5,849,732 | A | * | 12/1998 | Suzuki et al. | ................. 514/212 |
| 6,359,134 | B1 | * | 3/2002 | Tawada et al. | |

FOREIGN PATENT DOCUMENTS

| EP | 0540051 | 5/1993 |
| EP | 0 608 759 | 8/1994 |
| WO | 92 08709 | 5/1992 |
| WO | 93 22303 | 11/1993 |
| WO | 96/30347 | 10/1996 |
| WO | 97/02245 | * 1/1997 |

OTHER PUBLICATIONS

Tawada et al, *Chemical Abstracts*, vol. 130 No. 38404 (Abstract for WO 9854164, Dec. 3, 1998).*
Tadashi, et al, *Chemical Abstracts*, vol. 126, No. 157403 (Abstract for WO Jan. 23, 1997).*
Suzuki, et al, *Chemical Abstracts*, vol. 131, No. 49643. (Abstract for JP 11139969 May 25, 1999).*
Kobayashi et al, *Chemical Abstracts*, vol. 132, No. 194391 (Abstract for WO 00 09 480 Feb. 24, 2000).*
Eldred C D et al: "Orally Active Non–Peptide Fibrinogen Receptor (GpIIb/IIIa) Antagonists: Identification of 4-[4-[4-(Aminoiminomethyl)phenyl]-1-piperazinyl]-1-piperidineacetic Acid as a Long-Acting, Broad-Spectrum Antithrombotic Agent" J. Med. Chem. (JMCMAR, 00222623);94; vol. 37 (23); pp. 3882–3885, XP000579663 Glaxo Group Research Ltd.;Department of Medicinal Chemistry; Ware / Hertfordshire; SG12 ODP; UK (GB).
Stuerzebecher J et al; "Synthesis and Structure–Activity Relationships of Potent Thrombin Inhibitors: Piperazides of 3–Amidinophenylalanine" J. Med. Chem. (JMCMAR, 00222623);97; vol. 40 (19); pp. 3091–3099, XP002077904 Zentrum fuer Vaskulaere Biologie und Medizin;Klinikum der Friedrich–Schiller–Universitaet Jena; Erfurt; D–99089; Germany (DE).

* cited by examiner

Primary Examiner—Emily Bernhardt
(74) Attorney, Agent, or Firm—Millen, White, Zelano & Branigan, P.C.

(57) ABSTRACT

Novel compounds of the formula I

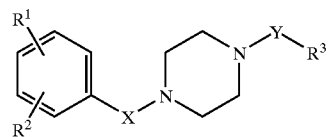

in which
X, Y, R$^1$, R$^2$ and R$^3$ are as defined in Patent Claim 1
are inhibitors of coagulation factor Xa and can be employed for the prophylaxis and/or therapy of thromboembolic disorders.

31 Claims, No Drawings

BENZAMIDINE DERIVATIVES AS FACTOR XA INHIBITORS

The invention relates to compounds of the formula I

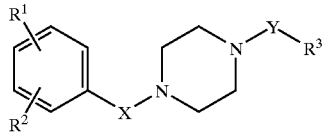

in which
R¹ is —C(=NH)—Nh₂ which can also be monosubstituted by —COA, —CO—[C(R⁶)₂]ₙ—Ar, —COOA, —OH or by a conventional amino-protective group,

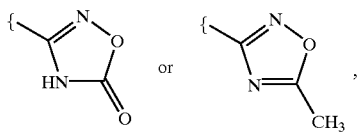

R² is H, A, OR⁶, N(R⁶)₂, NO₂, CN, Hal, NHCOA, NHCOAr, NHSO₂A, NHSO₂Ar, COOR⁶, CON(R⁶)₂, CONHAr, COR⁶, COAr, S(O)ₙA or S(O)ₙAr,
R³ is A, cycloalkyl, —[C(R⁶)₂]ₙAr, —[C(R⁶)₂]ₙ—O—Ar, —[C(R⁶)₂]ₙHet or —C(R⁶)₂=C(R⁶)₂—Ar,
R⁶ is H, A or benzyl,
X is absent, —CO—, —C(R⁶)₂—, —C(R⁶)₂—C(R⁶)₂—, —C(R⁶))₂—CO—, —C(R⁶)₂—C(R⁶)₂—CO—, —C(R⁶)=C(R⁶)—CO—, —NR⁶CO—, —N{[C(R⁶)₂]ₙ—COOR⁶}—O— or —C(COOR⁶) R⁶—O(R⁶)₂—CO—,
Y is —C(R⁶)₂—, —SO₂—, —CO—, —CO— or —CONR⁶—,
A is alkyl having 1–20 C atoms in which one or two CH₂ groups can be replaced by O or S atoms or by —CR⁶=CR⁶— groups and/or 1–7 H atoms can be replaced by F,
Ar is naphthyl or phenyl which is unsubstituted or mono-, di- or trisubstituted by A, Ar', OR⁶, N(R⁶)₂, NO₂, CN, Hal, NHCOA, NHCOAr', NHSO₂A, NHSO₂Ar', COOR⁶, CON(R⁶)₂, CONHAr', COR⁶, COAr', S(O)ₙA or S(O)ₙAr,
Ar' is naphthyl or phenyl which is unsubstituted or mono-, di- or trisubstituted by A, OR⁶, N(R⁶)₂, NO₂, CN, Hal, NHCOA, COOR⁶, CON(R⁶)₂, COR⁶ or S(O)ₙA,
Het is a mono- or bicyclic saturated or unsaturated heterocyclic ring system which contains one, two, three or four identical or different hetero atoms such as nitrogen, oxygen and sulphur and which is unsubstituted or mono- or polysubstituted by Hal, A, Ar', COOR⁶, CN, N(R⁶)₂, NO₂, Ar—CONH—OH₂ and/or carbonyl oxygen,
Hal is F, Cl, Br or I,
n is 0, 1 or 2,
and salts thereof.

The invention also provides the optically active forms, the racemates, the diastereomers and the hydrates and solvates of these compounds.

The invention was based on the object of discovering novel compounds having valuable properties, in particular those which can be used for preparing medicaments.

It has been found that the compounds of the formula I and their salts have very useful pharmacological properties, coupled with good tolerability. In particular, they have factor Xa-inhibiting properties and can therefore be employed for combating and preventing thromboembolic disorders such as thrombosis, myocardial infarction, arteriosclerosis, inflammations, apoplexy, angina pectoris, restenosis after angioplasty and claudicatio intermittens.

Aromatic amidine derivatives having antithrombotic action are known, for example, from EP 0 540 051 B1. Cyclic guanidines for the treatment of thromboembolic disorders are described, for example, in WO 97/08165. Aromatic heterocycles having factor Xa-inhibiting activity are known, for example, from WO 96/10022.

The antithrombotic and anticoagulant effect of the compounds according to the invention is attributed to the inhibiting action on the activated coagulation protease, known under the name factor Xa. Factor Xa is one of the proteases which is involved in the complex process of blood coagulation. Factor Xa catalyses the conversion of prothrombin into thrombin which in turn contributes to thrombus formation. An activation of thrombin can result in the occurrence of thromboembolic disorders. Inhibition of factor Xa can thus prevent thrombin formation. The compounds of the formula I according to the invention and their salts intervene in the blood coagulation process by inhibiting factor Xa and thus inhibit the formation of thrombi.

The inhibition of factor Xa by the compounds according to the invention and the measurement of the anti-coagulating and antithrombotic activity can be determined by customary in vitro or in vivo methods. A suitable method is described, for example, by J. Hauptmann et al. in Thrombosis and Haemostasis 63, 220–223 (1990).

The inhibition of factor Xa can be determined, for example, by the method of T. Hara et al. in Thromb. Haemoscas. 71, 314–319 (1994).

The compounds of the formula I can be employed as medicaments in human and veterinary medicine, in particular for combating and preventing thromboembolic disorders such as thrombosis, myoca-dial infarction, arteriosclerosis, inflammations, apoplexy, angina pectoris, restenosis after angioplasty and claudicatio intermittens.

The invention provides the compounds of the formula I and their salts, and also a process for preparing compounds of the formula I according to Claim 1 and their salts, characterized in that a) they are liberated from one of their functional derivatives by treatment with a solvolysing or hydrogenolysing agent, by
  i) liberating an amidino group from its oxadiazole derivative by hydrogenolysis,
  ii) replacing a conventional amino-protective group by treatment with a solvolysing or hydrogenolysing agent with hydrogen or liberating an amino group which is protected by a conventional protective group, or b) that for preparing compounds of the formula I in which $R^1$ is

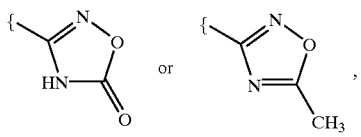

X is —CO— or —C(R)$_2$—CO—,
and $R^2$, $R^3$ and Y are as defined in Claim 1,
a compound of the formula II

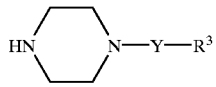

in which
$R^3$, $R^4$, $R^5$, W and Y are as defined in Claim 1,
is reacted with a compound of the formula III

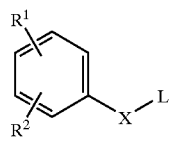

in which
$R^1$ is

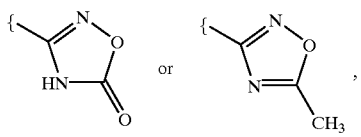

X is —CO— or —C(R$^6$)$_2$—CO—,
$R^2$ is as defined in Claim 1,
and L is Cl, Br, I or a free or a reactive functionally derivatized OH group, or c) that for preparing compounds of the formula I
in which
$R^1$ is

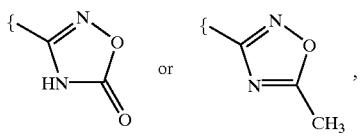

Y is —SO$_2$—, —CO—, —CO— or —C(R$^6$)$_2$—,
and $R^2$ and X are as defined in Claim 1,
a compound of the formula IV

L—Y—R$^3$    IV in which
Y is —SO$_2$—, —CO——CO— or —C(R$^6$)$_2$—,
$R^3$ is as defined in Claim 1, and L is Cl, Br, I or a free or a reactive functionally derivatized OH group, is reacted with a compound of the formula V

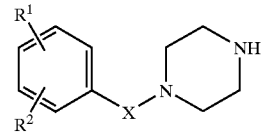

in which
$R^1$ is

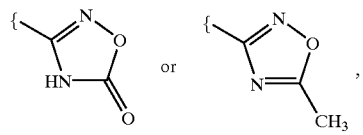

and $R^2$ and X are as defined in Claim 1, or
d) that for preparing compounds of the formula I
in which
$R^1$ is

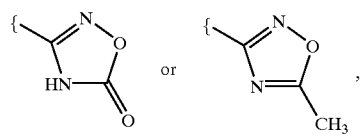

Y is —CONH—,
and $R^2$ and X are as defined in Claim 1,
a compound of the formula VI

R$^3$—N=C=O    VI in which
$R^3$ is as defined in Claim 1,
is reacted with a compound of the formula V

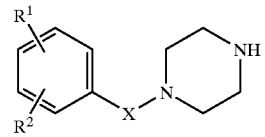

in which
$R^1$ is

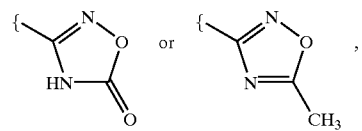

and $R^2$ and X are as defined in Claim 1, or
e) that for preparing compounds of the formula I
in which
$R^1$ is —C(=NH)—NH$_2$,
a cyano group is converted into an amidino group,
f) and/or that in a compound of the formula I, one or more radicals $R^1$, $R^2$ and/or $R^3$ are converted into one or more radicals $R^1$, $R^2$ and/or $R^3$ by, for example,
 i) hydrolysing an ester group to give a carboxyl group,
 ii) reducing a nitro group,
 iii) acylating an amino group,
g) and/or converting a base or acid of the formula I into one of its salts.

For all the radicals which occur several times, such as, for example, $R^6$, the meanings thereof are independent of one another.

Hereinabove and hereinbelow, the radicals or parameters L, X, Y, $R^1$, $R^2$ and $R^3$ have the meanings given for the formulae I to VI, unless expressly stated otherwise.

In the above formulae, A is alkyl and has 1 to 20, preferably 1, 2, 3, 4. 5, 6, 7, 8, 9, 10, 11 or 12 C atoms. A is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-,2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl, octyl, nonyl or decyl. Alkyl is furthermore, for example, trifluoromethyl, pentafluoroethyl, allyl or crotyl.

Cycloalkyl is preferably cyclopropyl, cyclobutyl, cyclopentyl, cyclohexyl or cycloheptyl. Cycloalkyl is in particular the radical of a bicyclic terpene, such as, for example, 3-menthyl; very particular preference is given to the camphor-10-yl radical.

$COR^6$ is acyl and is preferably formyl, acetyl, propionyl, furthermore also butyryl, pentanoyl or hexanoyl.

Hal is preferably F, Cl or Br, but also I.

$R^2$ is preferably H, fluorine, chlorine, bromine, iodine, hydroxyl, methoxy, ethoxy, propoxy, nitro, amino, methylamino, dimethylamino, ehylamino, diethyl-amino, acetamido, sulphonamido, methylsulphonamido, phenylsulphonamido, methylthio, ethylthio, methylsulphinyl, ethylsulphinyl, methylsulphonyl, ethylsulphonyl, phenylsulphinyl, phenylsulphonyl, cyano, carboxyl, methoxycarbonyl, ethoxycarbonyl, furthermore also acyl or benzoyl.

$R^3$ is preferably, for example, A, cycloalkyl, Ar, $CH_2Ar$, $CH_2OAr$, $CH_2CH_2Ar$, $CH_2Het$, $CH_2CH_2Het$ or $CH=CH$-Ar.

$R^6$ is H, A or benzyl, but preferably H.

X is preferably, for example, absent, —CO—, —$OH_2$—, —$CH_2$—$CH_2$—, —$CH_2$—CO—, —$CH_2$—$CH_2$—CO—, —CH=CH—CO—, —$NR^6CO$—, —N{$[CH_2]_n COOR^6$}—CO— or —$CH(COOR^6)$—$CH_2$—CO—.

Y is preferably, for example, —$SO_2$— or —CO—, furthermore also —COO—, —CONH— or —$CH_2$—.

Ar is preferably unsubstituted phenyl or naphthyl, furthermore preferably naphthyl or phenyl which is mono-, di- or trisubstituted, for example by A, fluorine, chlorine, bromine, iodine, hydroxyl, methoxy, ethoxy, propoxy, butoxy, pentyloxy, hexyloxy, benzyloxy, phenethyloxy, methylthio, ethylthio, methylsulphinyl, ethylsulphinyl, methylsulphonyl, ethylsulphonyl, phenylsulphinyl, phenylsulphonyl, nitro, amino, methylamino, ethylamino, dimethylamino, diethylamino, formamido, acetamido, propionylamino, butyrylamino, methylsulphonamido, ethylsulphonamido, propylsulphonamido, butylsulphonamido, phenylsulphonamido, (4-methylphenyl)sulphonamido, carboxymethoxy, carboxyethoxy, methoxycarbonylmethoxy, methoxycarbonyl-ethoxy, hydroxymethoxy, hydroxyethoxy, methoxyethoxy, carboxyl, methoxycarbonyl, ethoxycarbonyl, cyano, phenylaminocarbonyl, acyl or benzoyl, furthermore also biphenyl.

Ar is therefore preferably, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-acetamidophenyl, o-, m-or p-methoxyphenyl, o-, m- or p-ethoxyphenyl, o-, m- or p-carboxyphenyl, o-, m- or p-methoxycarbonylphenyl, o-, m- or p-(N,N-dimethylamino)phenyl, o-, m- or p-(N-ethylamino)phenyl, o-, m- or p-(N,N-diethylamino)phenyl, o-, m- or p-acetylphenyl, o-, m- or p-formylphenyl, o-, m- or p-fluorophenyl, o-, m- or p-bromophenyl, o-, m- or p-chlorophenyl, o-, m- or p-methylsulphonylphenyl, o-, m- or p-(phenyl-sulphonamido)phenyl, o-, m- or p-(methylsulphonamido)phenyl, o-, m- or p-methylthiophenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro-, or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar is very particularly preferably unsubstituted phenyl or naphthyl, furthermore preferably, for example, phenyl or naphthyl which is mono-, di- or trisubstituted by A, chlorine, methoxy, amino or dimethylamino, or is furthermore also biphenyl.

Ar' is in particular, for example, phenyl or naphthyl, furthermore preferably, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p- (N-methylamino)phenyl, o-, m- or p-acetamidophenyl, o-, m- or p-methoxyphenyl, o-, m- or p-ethoxyphenyl, o-, m- or p-carboxyphenyl, o-, m- or p-methoxycarbonylphenyl, o-, m- or p-(N,N-dimethylamino)phenyl, o-, m- or p-(N-ethylamino)phenyl, o-, nm- or p- (N,N-diethylamino)phenyl, o-, m- or p-acetylphenyl, o-, m- or p-formylphenyl, o-, m- or p-fluorophenyl, o-, m- or p-bromophenyl, o-, m- or p-chlorophenyl or c-, m- or p-methylsulphonylphenyl.

Het is preferably, for example, 2- or 3-furyl, 2- or 3-thienyl, 1-, 2- or 3-pyrrolyl, 1-, 2-, 4- or 5-.imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6-or 7-benzisoxazolyl, 2-, 4-, 5-, 6- or 7-benzothiazolyl, 2-, 4-, S-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo[(1,4]oxazinyl, furthermore preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl. The heterocyclic radicals may also be partially or fully hydrogenated. Het may also be, for example, 2,3-dihydro-2-, -3-, -4-or -5-furyl, 2,5-dihydro-2-, -3-, -4- or -5-furyl, tetrahydro-2- or -3-Furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -S-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3-or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo[1,4]oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxo-methylenedioxy)phenyl or else 3,4-dihydro-2H-1,5-benzodioxepin-6- or -7-yl, furthermore preferably 2,3-dihydrobenzofuranyl or 2,3-dihydro-2-oxofuranyl.

Het is unsubstituted or mono- or polysubstituted by Hal, A, Ar', COOR , CN, $N(R^6)_2$, $NO_2$, Ar—CONH—CH .

"Poly" means di, tri, tetra or penta.

The compounds of the formula I may have one or more chiral centres and may therefore be present in various stereoisomeric forms. The formula I embraces all of these forms.

Consequently, the invention provides in particular those compounds of the formula I in which at least one of the abovementioned radicals has one of the preferred meanings given above. Some preferred groups of compounds can be expressed by the following moieties Ia to If which correspond to the formula I and where the radicals which are not defined more specifically have the meaning given for the formula I, but where in Ia $R^1$ is —C(=NH)—$NH_2$, which can also be monosubstituted by —COA, —CO—$[C(R^6)_2]_n$—Ar, —COOA, —OH or by a conventional amino-protective group,

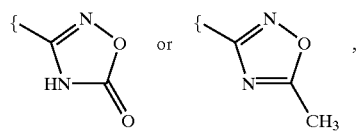

$R^2$ is H, A, $OR^6$, $N(R^6)_2$, $NO_2$, CN, Hal, NHCOA, NHCOAr, $NHSO_2A$, $NHSO_2Ar$, $COOR^6$, $CON(R^6)_2$, CONHAr, $COR^6$, COAr, $S(O)_nA$ or $S(O)_nAr$, $R^3$ is A, cycloalkyl, Ar, $CH_2Ar$, $CH_2OAr$, $CH_2CH_2Ar$, $CH_2Het$, $CH_2CH_2Het$ or CH=CH—Ar, $R^6$ is H or A, X is absent, —CO—, —$CH_2$—CO—, —$CH_2$—$CH_2$—CO—, —$CH_2$—, —$CH_2$—$CH_2$—, —CH=CH—CO—, —NHCO—, —N($CH_2COOR^6$)—CO— or —CH($COOR^6$)—$CH_2$—CO—, Y is —$SO_2$—, —CO—, —CO—, —CO—NH— or —$CH_2$—, A is alkyl having 1–20 C atoms in which one or two $CH_2$ groups may be replaced by O or S atoms or by —$CR^6$=$CR^6$— groups and/or 1–7 H atoms may be replaced by F, Ar is naphthyl or phenyl which is unsubstituted or mono-, di- or trisubstituted by A, Ar', $OR^6$, $N(R^6)_2$, $NO_2$, CN, Hal, NHCOA, NHCOAr', $NHSO_2A$, $NHSO_2Ar'$, $COOR^6$, $CON(R^6)_2$, CONHAr', $COR^6$, COAr', $S(O)_nA$ or $S(O)_nAr$, Ar' is naphthyl or phenyl which is unsubstituted or mono-, di- or trisubstituted by A, $OR^6$, $N(R^6)_2$, $NO_2$, CN, Hal, NHCOA, $COOR^6$, $CON(R^6)_2$, $COR^6$ or $S(O)_nA$, Het is a mono- or bicyclic saturated or unsaturated heterocyclic ring system which contains one, two, three or four identical or different hetero atoms such as nitrogen, oxygen and sulphur and which is unsubstituted or mono- or poly-substituted by Hal, A, Ar', $COOR^6$, CN, $N(R^6)_2$, $NO_2$, Ar—CONH—$CH_2$ and/or carbonyl oxygen, Hal is r, Cl, Br or I and n is 0, 1 or 2;

in Ib $R^1$ is —C(=NH)—NH2, which can also be monosubstituted by —COA, —CO—$[C(R^6)_2]_n$—Ar, —COOA, —OH or by a conventional amino-protective group,

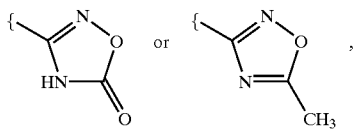

$R^2$ is H, $R^3$ is A, cycloalkyl, Ar, —$CH_2Ar$, —$CH_2OAr$, —$CH_2CH_2Ar$, —$CH_2Het$, —$CH_2CH_2Het$ or —CH=CH—Ar, $R^6$ is H or A, X is absent, —CO—, —$CH_2$—CO—, —$CH_2$—$CH_2$—CO—, —$CH_2$—, —$CH_2$—$CH_2$—, —CH=CH—CO—, —NHCO—, —N($CH_2COOR^6$)—CO— or —CH($COOR^6$)—$CH_2$—CO—, Y is —$SO_2$—, —CO—, —CO—, —CO—NH— or —$CH_2$—, A is alkyl having 1–20 C atoms in which one or two $CH_2$ groups may be replaced by O or S atoms or by —$CR^6$=$CR^6$— groups and/or 1–7 H atoms may be replaced by F, Ar is naphthyl or phenyl which is unsubstituted or mono-, di- or trisubstituted by A, Ar', $OR^6$, $NH_2$, $NO_2$, CN, Hal, NHCOA, NHCOAr', $NHSO_2A$, $NHSO_2Ar'$, $COOR^6$, $CON(R^6)_2$, CONHAr', $COR^6$, COAr', $S(O)_nA$ or $S(O)_nAr$, Ar' is naphthyl or phenyl which is unsubstituted or mono-, di- or trisubstituted by A, $OR^6$, $N(R^6)_2$, $NO_2$, CN, Hal, NHCOA, $COOR^6$, $CON(R^6)_2$, $COR^6$ or $S(O)_nA$, Het is a mono- or bicyclic saturated or unsaturated heterocyclic ring system which contains one, two, three or four identical or different hetero atoms such as nitrogen, oxygen and sulphur and which is unsubstituted or mono- or poly-substituted by Hal, A, Ar', $COOR^6$, CN, $N(R^6)_2$, $NO_2$, Ar—CONH—$CH_2$ and/or carbonyl oxygen, Hal is F, Cl, Br or I and n is 0, 1 or 2;

in Ic $R^1$ is —C(=NH)—$NH_2$, which can also be monosubstituted by —COA, —CO—$[C(R^6)_2]_n$—Ar, —COOA, —OH or by a conventional amino-protective group,

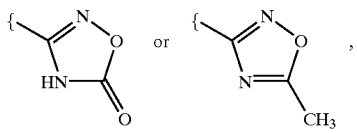

R² is H,

R³ is A, cycloalkyl, Ar, —CH₂Ar, —CH₂OAr, —CH₂CH₂Ar, —CH₂Het, —CH₂CH₂Het or —CH=CH—Ar, R⁶ is H or A, X is absent, —CO—, —CH₂—CO—, —CH₂—CH₂—CO—, —CH₂—, —CH₂—CH₂—, —CH=CH—CO—, —NHCO—, —N{CH₂—COOR⁶}—CO— or —CH(COOR )—CH₂—CO—, Y is —SO₂—, —CO—, —CO—, —CO—NH— or —CH₂—, A is alkyl having 1–20 C atoms in which one or two CH₂ groups may be replaced by O or S atoms or by —CR⁶=CR⁶— groups and/or 1–7 H atoms may be replaced by F, Ar is naphthyl or phenyl which is unsubstituted or mono-, di- or trisubstituted by A, Ar', OR⁶, N(R⁵)₂, NO₂, CN, Hal, NHCOA, NHCOAr', NHSO₂A, NHSO₂Ar', COOR⁶, CON(R⁶)₂, CONHAr', COR⁶, COAr', S(O)ₙA or S(O)ₙAr, Ar' is naphthyl or phenyl which is unsubstituted or mono-, di- or trisubstituted by A, OR⁶, N(R⁶)₂, NO₂, CN, Hal, NHCOA, COOR⁶, CON(R⁶)₂, COR⁶ or S(O)ₙA, Het is a mono- or bicyclic heterocyclic ring system which is unsubstituted or mono- or polysubstituted by Hal, A, Ar', COOR⁶, CN, N(R⁶)₂, NO₂, Ar—CONH—CH₂ and/or carbonyl oxygen selected from the group consisting of thiophene, tetrahydroquinoline, chroman, pyrazole, isoxazole, pyridine, benzodioxole or benzothiophene, Hal is F, Cl, Br or I and n is 0, 1 or 2;

in Id

R¹ is —C(=NH)—NH₂, which can also be monosubstituted by —COA, —CO—[C(R⁶)₂]ₙ—Ar, —COOA, —OH or by a conventional amino-protective group,

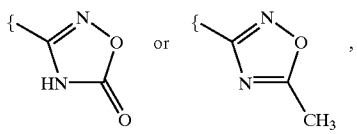

R² is H,

R³ is A, cycloalkyl, Ar, —CH₂Ar, —CH₂OAr, —CH₂CH₂Ar, —CH₂Het, —CH₂CH₂Het or —CH=CH—Ar, R⁶ is H or A, X is absent, —CO—, —CH₂—CO—, —CH₂—CH₂—CO—, —CH₂—, —CH₂—CH₂—, —CH=CH—CO—, —NHCO—, —N{CH₂—COOR⁶}—CO— or —CH(COOR⁶)—CH₂—CO—, Y is —SO₂—, —CO—, —CO—NH— or —CH₂—, A is alkyl having 1–20 C atoms in which one or two CH₂ groups may be replaced by O or S atoms or by —CR⁶=CR⁶— groups and/or 1–7 H atoms may be replaced by F, Ar is naphthyl or phenyl which is unsubstituted or mono-, di- or trisubstituted by A, Ar', OR⁶, N(R⁶)₂, NO₂, CN, Hal, NHCOA, NHCOAr', NHSO₂A, NHSO₂Ar', COOR⁶, CON(R⁶)₂, CONHAr', COR⁶, COAr', S(O)ₙA or S(O)ₙAr, Ar' is phenyl, Het is a mono- or bicyclic heterocyclic ring system which is unsubstituted or mono- or polysubstituted by Hal, A, Ar', COOR⁶, CN, N(R⁶)₂, NO₂, Ar—CONH—CH₂ and/or carbonyl oxygen selected from the group consisting of thiophene, tetrahydroquinoline, chroman, pyrazole, isoxazole, pyridine, benzodioxole, benzothiophene or dibenzofuran, Hal is F, Cl, Br or I and n is 0, 1 or 2;

in Ie

R¹ is —C(=NH,)—NH₂, which can also be monosubstituted by —COA, —CO—[C(R⁶)₂]ₙ—Ar, —COOA, —OH or by a conventional amino-protective group,

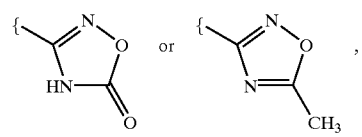

R² is H,

R³ is A, cycloalkyl, Ar, CH₂Ar, CH₂OAr, CH₂CH₂Ar, CH₂Het, CH₂CH₂Het or CH=CH—Ar, R⁶ is H or A, X is absent, —CO—, —CH₂—CO—, —CH₂—CH₂—CO—, —CH₂—, —CH₂—CH₂—, —NHCO—, —N{CH₂—COOR⁶}—CO— or —CH(COOR⁶)—CH₂—CO—, Y is —SO₂—, —CO— or —CH₂—, A is alkyl having 1–20 C atoms in which one or two CH₂ groups may be replaced by O or S atoms or by —CR⁶=CR 6— groups and/or 1–7 H atoms may be replaced by F, Ar is naphthyl or phenyl which is unsubstituted or mono-, di- or trisubstituted by A, Ar', OR⁶, N(R⁶)₂, NO₂, CN, Hal, NHCOA, NHCOAr', NHSO₂A, NHSO₂Ar', COOR⁶, CON(R⁶)₂, CONHAr', COR⁶, COAr', S(O)ₙA or S(O)ₙAr, Ar' is phenyl, Het is a mono- or bicyclic heterocyclic ring system which is unsubstituted or mono- or polysubstituted by Hal, A, Ar', COOR⁶, CN, N(R⁶)₂, NO₂, Ar—CONH—CH₂ and/or carbonyl oxygen selected from the group consisting of thiophene, tetrahydroquinoline, chroman, pyrazole, isoxazole, pyridine, benzodioxole, benzothiophene or dibenzofuran, Hal is F, Cl, Br or I and n is 0, 1 or 2;

in If

R¹ is —C(=NH)—NH₂ which can also be monosubstituted by COOA,

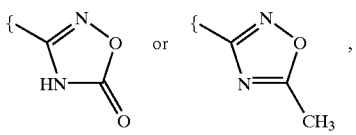

$R^2$ is H, $R^3$ is A, cycloalkyl, Ar, —CH$_2$Ar, —CH$_2$OAr, —CH$_2$CH$_2$Ar, —CH$_2$Het, —CH$_2$CH$_2$Het or —CH=CH—Ar, $R^6$ is H or A, X is absent, —CO—, —CH$_2$—CO—, —CH$_2$—CH$_2$—CO—, —CH$_2$—, —CH$_2$—CH$_2$—, —NHCO—, —N{(CH$_2$—COOR$^6$)—CO— or —CH(COOR$^6$)—CH$_2$—CO—, Y is —SO$_2$—, —CO— or —CH$_2$—, A is alkyl having 1–20 C atoms in which one or two CH$_2$ groups may be replaced by O or S atoms or by —CR$^6$=CR$^6$— groups and/or 1–7 H atoms may be replaced by F, Ar is naphthyl or phenyl which is unsubstituted or mono-, di- or trisubstituted by A, Ar', OR$^6$, N(R$^6$)$_2$, NO$_2$, CN, Hal, NHCOA, NHCOAr', NHSO$_2$A, NHSO$_2$Ar', COOR$^6$, CON(R$^6$)$_2$, CONHAr', COR$^6$, COAr', S(O)$_n$A or S(O)$_n$Ar, Ar' is phenyl, Het is a mono- or bicyclic heterocyclic ring system which is unsubstituted or mono- or polysubstituted by Hal, A, Ar', COOR$^6$, CN, N(R )$_2$, NO$_2$, Ar—CONH—CH$_2$ and/or carbonyl oxygen selected from the group consisting of thiophene, tetrahydroquinoline, chroman, pyrazole, isoxazole, pyridine, benzodioxole, benzothiophene or dibenzofuran, Hal is F, Cl, Br or I and n is 0, 1 or 2.

The compounds of the formula I and also the starting materials for their preparation are otherwise prepared by methods known per se, such as are described in the literature (for example in the standard works such as Houben-Weyl, Methoden der organischen Chemie [Methods of Organic Chemistry], Georg-Thieme-Verlag, Stuttgart), and in particular under the reaction conditions which are known and suitable for the reactions mentioned. In these reactions, variants which are known per se and are not mentioned here in more detail can also be utilized.

If desired, the starting materials can also be formed in situ, so that they are not isolated from the reaction mixture but are immediately reacted further to give the compounds of the formula I.

Compounds of the formula I can preferably be obtained by liberating the compounds of the formula I from one of their functional derivatives by treatment with a solvolysing or hydrogenolysing agent.

Preferred starting materials for the solvolysis or hydrogenolysis are those which otherwise correspond to the formula I but, instead of one or more free amino and/or hydroxyl groups, contain corresponding protected amino and/or hydroxyl groups, preferably those which, instead of an H atom which is bonded to an N atom, carry an amino-protective group, in particular those which, instead of an HN group, carry an R'-N group, in which R' is an amino-protective group, and/or those which, instead of the H atom of a hydroxyl group, carry a hydroxyl-protective group, for example those which correspond to the formula I but, instead of a —COOH group, carry a group —COOR", in which R" is a hydroxyl-protective group.

Preferred starting materials also include the oxadiazole derivatives which can be converted into the corresponding amidino compounds.

The introduction of the oxadiazole group is effected, for example, by reacting the cyano compounds with hydroxylamine and reaction with phosgene, dialkyl carbonate, chloroformic ester, N,N'-carbonyldiimidazole or acetic anhydride.

It is also possible for several—identical or different—protected amino and/or hydroxyl groups to be present in the molecule of the starting material. If the protective groups present differ from one another, in many cases they can be cleaved off selectively.

The term "amino-protective group" is generally known and relates to groups which are suitable for protecting (blocking) an amino group from chemical reactions but which can easily be removed after the desired chemical reaction has been carried out at other sites of the molecule. Typical such groups are, in particular, unsubstituted or substituted acyl, aryl, aralkoxymethyl or aralkyl groups. Since the amino-protective groups are removed after the desired reaction (or reaction sequence), their nature and size is otherwise not critical; however, those having 1–20, in particular 1–8 C atoms are preferred. The term "acyl group" is to be interpreted in the broadest sense in connection with the present process. It includes acyl groups derived from aliphatic, araliphatic, aromatic or heterocyclic carboxylic acids or sulphonic acids, and in particular alkoxycarbonyl, aryloxycarbonyl and, above all, aralkoxycarbonyl groups. Examples of such acyl groups are alkanoyl, such as acetyl, propionyl or butyryl; aralkanoyl, such as phenylacetyl; aroyl, such as benzoyl or toluyl; aryloxyalkanoyl, such as POA; alkoxycarbonyl, such as methoxycarbonyl, ethoxycarbonyl, 2,2,2-trichloroethoxycarbonyl, BOC (tert-butyloxycarbonyl), 2-iodoethoxycarbonyl; aralkyloxycarbonyl such as CBZ ("carbobenzoxy"), 4-methoxybenzyloxycarbonyl, FMOC; arylsulphonyl such as Mtr. Preferred amino-protective groups are BOC and Mtr, and furthermore CBZ, Fmoc, benzyl and acetyl.

The term "hydroxyl-protective group" is also generally known and relates to groups which are suitable for protecting a hydroxyl group from chemical reactions but which can easily be removed after the desired chemical reaction has been carried out at other sites of the molecule. Typical such groups are the abovementioned unsubstituted or substituted aryl, aralkyl or acyl groups, and furthermore also alkyl groups. The nature and the size of the hydroxyl-protective groups is not critical, since they are removed again after the desired chemical reaction or reaction sequence; groups having 1–20, in particular 1–10 C atoms are preferred. Examples of hydroxyl-protective groups are, inter alia, benzyl, p-nitrobenzoyl, p-toluenesulphonyl, tert-butyl and acetyl, benzyl and tert-butyl being particularly preferred.

The liberation of the compounds of the formula I from their functional derivatives is effected—depending on the protective group used—for example with strong acids, expediently with TFA or perchloric acid, but also with other strong inorganic acids, such as hydrochloric acid or sulphuric acid, strong organic carboxylic acids, such as trichloroacetic acid, or sulphonic acids, such as benzene- or p-toluenesulphonic acid. The presence of an additional inert solvent is possible but not always necessary. Suitable inert solvents are, preferably, organic solvents, for example carboxylic acids, such as acetic acid, ethers, such as tetrahydrofuran or dioxane, amides, such as DMF, halogenated hydrocarbons, such as dichloromethane, or furthermore also alcohols, such as methanol, ethanol or isopropanol, and water. Mixtures of the abovementioned solvents are furthermore possible. TFA is preferably used in excess without addition of a further solvent, and perchloric acid is used in the form of a mixture of acetic acid and 70% perchloric acid in a ratio of 9:1. The reaction temperatures for the cleavage are expediently between about 0 and about 50°, and the reaction is preferably carried out at between 15 and 30° (room temperature).

The groups BOC, OBut and Mtr can preferably be cleaved off, for example, with TFA in dichloromethane or with about 3 to 5N HCl in dioxane at 15–30°, and the FMOC group can be cleaved off with an approximately 5 to 50% solution of dimethylamine, diethylamine or piperidine in DMF at 15–30°.

Protective groups which can be removed by hydrogenolysis (for example CBZ, benzyl or the liberation of the amidino group from its oxadiazole derivative) can be cleaved off, for example, by treatment with hydrogen in the presence of a catalyst (for example a noble metal catalyst, such as palladium, expediently on a support, such as carbon). Suitable solvents for this reaction are those mentioned above, in particular, for example, alcohols, such as methanol or ethanol, or amides, such as DMF. The hydrogenolysis is generally carried out at temperatures between about 0 and 100° under pressures between about 1 and 200 bar, preferably at 20–30° and 1–10 bar. Hydrogenolysis of the CBZ group is effected readily, for example, on 5–10% Pd/C in methanol or with ammonium formate (instead of hydrogen) on Pd/C in methanol/DMF at 20–30°.

Compounds of the formula I
in which
R¹ is

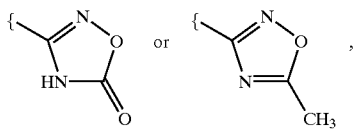

X is —CO— or —C(R⁶)₂—CO—,
and R², R³ and Y are as defined in Claim 1,
can preferably be obtained by reacting compounds of the formula II with compounds of the formula III.

In the compounds of the formula III, L is preferably Cl, Br, I or a reactively modified OH group, such as, for example, an activated ester, an imidazolide or alkylsulphonyloxy having 1–6 C atoms (preferably methylsulphonyloxy), or arylsulphonyloxy having 6–10 C atoms (preferably phenyl- or p-tolylsulphonyloxy).

The reaction is generally carried out in an inert solvent, in the presence of an acid binder, preferably an alkali metal hydroxide, carbonate or bicarbonate or an alkaline earth metal hydroxide, carbonate or bicarbonate, or of another salt of a weak acid of the alkali metals or alkaline earth metals, preferably of potassium, sodium, calcium or caesium. The addition of an organic base such as triethylamine, dimethylaniline, pyridine or quinoline or of an excess of the amine component of the formula II or of the alkylation derivative of the formula III may also be favourable. Depending on the conditions used, the reaction time is between several minutes and 14 days, the reaction temperature is between approximately 0° and 150°, usually between 20° and 130°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetra-chloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether (methylglycol or ethylglycol) or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulphoxides, such as dimethyl sulphoxide (DMSO); carbon disulphide; carboxylic acids, such as formic acid or acetic acid; nitro compounds, such as nitromethane or nitrobenzene; esters, such as ethyl acetate, or mixtures of the solvents mentioned.

The starting materials of the formulae II and III are generally known. Those which are novel, however, can be prepared by methods known per se.

Compounds of the formula I
in which
R¹ is

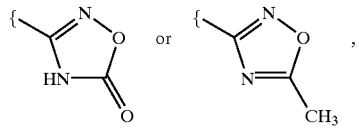

Y is SO₂, CO or COO,
and R² and X are as defined in Claim 1,
can preferably be obtained by reacting compounds of the formula IV with compounds of the formula V.

In the compounds of the formula IV L is preferably Cl, Br, I or a reactively modified OH group, such as, for example, an activated ester, an imidazolide or alkylsulphonyloxy having 1–6 C atoms (preferably methylsulphonyloxy), or arylsulphonyloxy having 6–10 C atoms (preferably phenyl- or p-tolylsulphonyloxy).

The reaction of the compounds of the formula IV with compounds of the formula V is preferably carried out in an inert solvent, with addition of a base and at temperatures as indicated above.

The starting materials of the formulae IV and V are generally known. Those which are novel, however, can be prepared by methods known per se.

Compounds of the formula I
in which
R¹ is

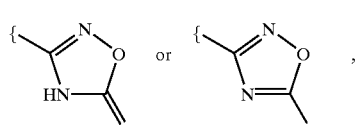

Y is CONH,
and R² and X are as defined in Claim 1,
can preferably be obtained by reacting compounds of the formula VI with compounds of the formula V.

The reaction of the compounds of the formula VI with compounds of the formula V is preferably carried out in an inert solvent and at temperatures as indicated above.

The starting materials of the formula VI are generally known. Those which are novel, however, can be prepared by methods which are known per se.

Compounds of the formula I in which $R^1$ is —C(=NH)—$NF_2$ can furthermore be obtained from the corresponding cyano compound.

The conversion of a cyano group into an amidino group is carried out by reaction with, for example, hydroxylamine and subsequent reduction of the N-hydroxamidine with hydrogen in the presence of a catalyst, such as, for example, Pd/C.

To prepare an amidine of he formula I ($R^1$=—C(=NH)—$NH_2$), ammonia can also be added onto a nitrile of the formula I ($R^1$=CN). The addition is preferably carried out in several stages by a procedure in which, in a manner known per se, a) the nitrile is converted with $H_2S$ into a thioamide, which is converted with an alkylating agent, for example $CH_3I$, into the corresponding S-alkyl-imidothioester, which in turn reacts with $NF_3$ to give the amidine, b) the nitrile is converted with an alcohol, for example ethanol, in the presence of HCl into the corresponding imidoester, and this is treated with ammonia, or c) the nitrile is reacted with lithium bis(trimethylsilyl)amide and the product is then hydrolysed.

Furthermore, it is possible to convert a compound of the formula I into another compound of the formula I by converting one or more radicals $R^1$, $R^2$ $R^3$ $R^4$ and/or $R^5$ into one or more radicals $R^1_1$ $R^2$, $R^3$, $R^4$ and/or $R^5$, for example by reducing nitro groups (for example by hydrogenation over Raney nickel or Pd/carbon in an inert solvent, such as methanol or ethanol) to amino groups.

Esters can be hydrolysed, for example with acetic acid or with NaOH or KOH in water, water-THF or water-dioxane at temperatures between 0 and 100°.

It is furthermore possible to acylate free amino groups in a customary manner with an acyl chloride or acid anhydride or to alkylate with an unsubstituted or substituted alkyl halide, expediently in an inert solvent, such as dichloromethane or THF, and/or in the presence of a base, such as triethylamine or pyridine, at temperatures between −60 and +30°.

A base of the formula I can be converted into the associated acid addition salt with an acid, for example by reaction of equivalent amounts of the base and the acid in an inert solvent, such as ethanol, and subsequent evaporation. Acids which give physiologically acceptable salts are particularly suitable for this reaction. Thus, it is possible to use inorganic acids, for example sulphuric acid, nitric acid, hydrohalic acids, such as hydrochloric acid or hydrobromic acid, phosphoric acids, such as orthophosphoric acid, sulphaminic acid, or furthermore organic acids, in particular aliohatic, alicyclic, araliphatic, aromatic or heterocyclic mono- or polybasic carboxylic, sulphonic or sulphuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulphonic acid, ethanedisulphonic acid, 2-hydroxyethanesulphonic acid, benzenesulphonic acid, p-toluenesulphonic acid, naphthalene-mono- or -disulphonic acids and laurylsulphuric acid. Salts with physiologically unacceptable acids, for example picrates, can be used for isolation and/or purification of the compounds of the formula I.

On the other hand, compounds of the formula I can be converted with bases (for example sodium hydroxide, potassium hydroxide, sodium carbonate or potassium carbonate) into the corresponding metal, in particular alkali metal or alkaline earth metal salts or into the corresponding ammonium salts.

Owing to their molecular structure, the compounds of the formula I according to the invention can be chiral and can consequently be present in various enantiomeric forms. They may therefore be present in racemic or in optically active form.

Since the pharmaceutical activity of the racemates and/or the stereoisomers of the compounds according to the invention may differ, it may be desirable to use the enantiomers. In these cases, the end product or even the intermediates may be separated into enantiomeric compounds using chemical or physical means known to the person skilled in the art, or they may even be employed as such in the synthesis.

In the case of racemic amines, diastereomers are formed from the mixture by reaction with an optically active separating agent. Suitable separating agents are, for example, optically active acids, such as the R- and S-forms of tartaric acid, diacetyltartaric acid, dibenzoyltartaric acid, mandelic acid, malic acid, lactic acid, suitable N-protected amino acids (for example N-benzoylproline or N-benzenesulphonylproline) or the various optically active camphorsulphonic acids. A chromatographic separation of the enantiomers can also be advantageously carried out with the aid of an optically active separating agent (for example dinitrobenzoylphenylglycine, cellulose triacetate or other carbohydrate derivatives or chiral derivatized methacrylate polymers immobilized on silica gel). Solvents which are suitable for this purpose are aqueous or alcoholic solvent mixtures, such as, for example, hexane/isopropanol/acetonitrile, for example in the ratio 82:15:3.

The invention furthermore provides the use of the compounds of the formula I and/or their physiologically acceptable salts for the preparation of pharmaceutical formulations, in particular by a non-chemical route. For this purpose, they can be brought into a suitable dosage form together with at least one solid, liquid and/or semi-liquid carrier or auxiliary, and if appropriate in combination with one or more further active compounds.

The invention furthermore provides pharmaceutical formulations comprising at least one compound of the formula I and/or one of its physiologically acceptable salts.

These formulations can be used as medicaments in human or veterinary medicine. Possible carriers are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc and petroleum jelly. Tablets, pills, coated tablets, capsules, powders, granules, syrups, juices or drops are used, in particular, for oral administration, suppositories are used for rectal administration, solutions, preferably oily or aqueous solutions, and furthermore suspensions, emulsions or implants are used for parenteral administration, and ointments, creams or powders are used for topical administration. The novel compounds can also be lyophilized and the resulting lyophilisates can be used, for example, for the preparation of injection formulations. The formulations mentioned can be sterilized and/or comprise auxiliaries, such as lubricants, preservatives, stabilizers and/or wetting agents, emulsifiers, salts for influencing the osmotic pressure, buffer substances, dyestuffs, flavourings and/or several further active compounds, for example one or more vitamins.

The compounds of the formula I and their physiologically acceptable salts can be employed for combating and preventing thromboembolic disorders, such as thrombosis, myocardial infarction, arteriosclerosis, inflammations, apoplexy, angina pectoris, restenosis after angioplasty and claudicatio intermittens. For this purpose, the substances according to the invention are usually preferably administered in dosages of between about 1 and 500 mg, in particular between 5 and 100 mg per dosage unit. The daily dosage is preferably between about 0.02 and 10 mg/kg of body weight. However, the specific dose for each patient depends on the most diverse factors, for example on the activity of the specific compound employed, on the age, body weight, general state of health, sex, diet, on the administration time and route, and on the rate of excretion, medicament combination and severity of the particular disease to which the therapy applies. Oral administration is preferred.

All temperatures hereinabove and hereinbelow are given in ° C. In the following examples, "customary work-up" means: water is added, if necessary, the pH is brought to values of between 2 and 10, if necessary, depending on the structure of the end product, the mixture is extracted with ethyl acetate or dichloromethane, the organic phase is separated off, dried over sodium sulphate and evaporated and the residue is purified by chromatography over silica gel and/or crystallization. Rf values are for silica gel; mobile phase: ethyl acetate/methanol 9:1.

Mass spectrometry (MS):
EI (electron impact ionization) M$^+$
FAB (fast atom bombardment) (M+H)$^+$

EXAMPLE 1

46 ml of thionyl chloride and 1 ml of DMF are added to a solution of 10.0 g of 4-(5-methyl-1,2,4-oxadiazol-3-yl) benzoic acid in 150 ml of toluene. The solution is heated under reflux for 5 hours. The solvent is removed, giving 4-(5-methyl-1,2,4-oxadiazol-3-yl)-benzoyl chloride, EI 222. Subsequent reaction with 9.3 g of 1-tert-butoxycarbonylpiperazine in 150 ml of dichloromethane and 48 ml of triethylamine gives, after customary work-up, tert-butyl 4-[4-(5-methyl-[1,2,4]oxadiazol-3-yl)benzoyl] piperazine-1-carboxylate, FAB 373.

The BOC group is cleaved off using 4N HCl in dioxane. A solution of 100 mg of the resulting [4-(5-methyl-[1,2,4] oxadiazol-3-yl)phenyl]piperazin-1-ylmethanone ("A") and 120 mg of 6-chloronaphthalene-2-sulphonyl chloride in 5 ml of dichloromethane is admixed with 400 mg of 4-dimethylaminopyridine on polystyrene, and the mixture is stirred at room temperature For 18 hours. Filtration and removal of the solvent gives [4-(6-chloronaphthalene-2-sulphonyl)piperazin-1-yl][4-(5-methyl[1,2,4]oxadiazol-3-yl)phenyl]methanone, FAB 497.

Similarly, reaction of "A"
with 4-biphenylyl-2-sulphonyl chloride gives
[4-(4-biphenylylsulphonyl)piperazin-1-yl][4-(5-methyl[1,2,4]oxadiazol-3-yl)phenyl]methanone;
with 2-naphthylsulphonyl chloride gives
[4-(2-naphthylsulphonyl)piperazin-1-yl][4-(5-methyl[1,2,4]oxadiazol-3-yl)phenyl]methanone;
with 4-propylphenylsulphonyl chloride gives
[4-(4-propylphenylsulphonyl)piperazin-1-yl][4-(5-methyl[1,2,4]oxadiazol-3-yl)phenyl]methanone;
with 2-phenylvinylsulphonyl chloride gives
[4-(2-phenylvinylsulphonyl)piperazin-1-yl][4-(5-methyl[1,2,4]oxadiazol-3-yl)phenyl]methanone;
with 3-nitro-4-chlorophenylsulphonyl chloride gives
[4-(3-nitro-4-chlorophenylsulphonyl)piperazin-1-yl][4-(5-methyl[1,2,4]oxadiazol-3-yl)phenyl]methanone;
with 2-nitro-4-methoxyphenylsulphonyl chloride gives
[4-(2-nitro-4-methoxyphenylsulphonyl)piperazin-1-yl][4-(5-methyl[1,2,4]oxadiazol-3-yl)phenyl]methanone;
with p-tolylsulphonyl chloride gives
[4-(4-tolylsulphonyl)piperazin-1-yl][4-(5-methyl[1,2,4]oxadiazol-3-yl)phenyl]methanone;
with decylsulphonyl chloride gives
[4-(decylsulphonyl)piperazin-1-yl][4-(5-methyl[1,2,4]oxadiazol-3-yl)phenyl]methanone;
with benzylsulphonyl chloride gives
[4-(benzylsulphonyl)piperazin-1-yl][4-(5-methyl[1,2,4]oxadiazol-3-yl)phenyl]methanone;
with 3-nitro-6-methylbenzylsulphonyl chloride gives
[4-(3-nitro-6-methylbenzylsulphonyl)piperazin-1-yl][4-(5-methyl[1,2,4]oxadiazol-3-yl)phenyl]methanone;
with 2,3-dichlorophenylsulphonyl chloride gives
[4-(2,3-dichlorophenylsulphonyl)piperazin-1-yl][4-(5-methyl[1,2,4]oxadiazol-3-yl)phenyl]methanone;
with 3,4-dichlorophenylsulphonyl chloride gives
[4-(3,4-dichlorophenylsulphonyl)piperazin-1-yl][4-(5-methyl[1,2,4]oxadiazol-3-yl)phenyl]methanone;
with phenylsulphonyl chloride gives
[4-(phenylsulphonyl)piperazin-1-yl][4-(5-methyl[1,2,4]oxadiazol-3-yl)phenyl]methanone;
with 3-bromophenylsulphonyl chloride gives
[4-(3-bromophenylsulphonyl)piperazin-1-yl][4-(5-methyl[1,2,4]oxadiazol-3-yl)phenyl]methanone;
with 3,4-dimethoxyphenylsulphonyl chloride gives
[4-(3,4-dimethoxyphenylsulphonyl)piperazin-1-yl][4-(5-methyl[1,2,4]oxadiazol-3-yl)phenyl]methanone;
with 4-acetamido-3-chlorophenylsulphonyl chloride gives
[4-(4-acetamido-3-chlorophenylsulphonyl)piperazin-1-yl][4-(5-methyl[1,2,4]oxadiazol-3-yl)phenyl]methanone;
with 4-chloro-2,5-dimethoxyphenylsulphonyl chloride gives
[4-(4-chloro-2,5-dimethylphenylsulphonyl)piperazin-1-yl][4-(5-methyl[1,2,4]oxadiazol-3-yl)phenyl]methanone;
with m-tolylsulphonyl chloride gives
[4-(3-tolylsulphonyl)piperazin-1-yl][4-(5-methyl[1,2,4]oxadiazol-3-yl)phenyl]methanone;
with 2-methoxy-5-methylphenylsulphonyl chloride gives
[4-(2-methoxy-5-methylphenylsulphonyl)piperazin-1-yl][4-(5-methyl[1,2,4]oxadiazol-3-yl)phenyl]methanone;
with 3-chlorophenylsulphonyl chloride gives
[4-(3-chlorophenylsulphonyl)piperazin-1-yl][4-(5-methyl[1,2,4]oxadiazol-3-yl)phenyl]methanone;
with 4-methoxyphenylsulphonyl chloride gives
[4-(4-methoxyphenylsulphonyl)piperazin-1-yl][4-(5-methyl[1,2,4]oxadiazol-3-yl)phenyl]methanone;
with 2-thienylsulphonyl chloride gives
[4-(2-thienylsulphonyl)piperazin-1-yl][4-(5-methyl[1,2,4]oxadiazol-3-yl)phenyl]methanone;
with 4-chlorophenylsulphonyl chloride gives
[4-(4-chlorophenylsulphonyl)piperazin-1-yl][4-(5-methyl[1,2,4]oxadiazol-3-yl)phenyl]methanone;
with isopropylsulphonyl chloride gives
[4-(isopropylsulphonyl)piperazin-1-yl][4-(5-methyl[1,2,4]oxadiazol-3-yl)phenyl]methanone;
with 8-quinolylsulphonyl chloride gives
[4-(quinolylsulphonyl)piperazin-1-yl][4-(5-methyl[1,2,4]oxadiazol-3-yl)phenyl]methanone;
with 4-nitrophenylsulphonyl chloride gives
[4-(4-nitrophenylsulphonyl)piperazin-1-yl][4-(5-methyl[1,2,4]oxadiazol-3-yl)phenyl]methanone;
with 3-chloro-6-methoxyphenylsulphonyl chloride gives
[4-(3-chloro-6-methoxyphenylsulphonyl)piperazin-1-yl][4-(5-methyl[1,2,4]oxadiazol-3-yl)phenyl]methanone;

with 4-acetamidophenylsulphonyl chloride gives
[4-(4-acetamidophenylsulphonyl)piperazin-1-yl][4-(5-methyl[1,2,4]oxadiazol-3-yl)phenyl]methanone;
with 2,2,5,7,8-pentamethylchroman-6-ylsulphonyl chloride gives
[4-(2,2,5,7, 8-pentamethylchroman-6-ylsulphonyl)piperazin-1-yl][4-(5-methyl[1,2,4]oxadiazol-3-yl)phenyl]methanone;
with camphor-10-ylsulphonyl chloride gives
[4-(camphor-10-ylsulphonyl)piperazin-1-yl][4-(5-methyl[1,2,4]oxadiazol-3-yl)phenyl]methanone;
with 5-(1-methyl-5-trifluoromethyl-3-pyrazolyl)-2-thienylsulphonyl chloride gives
{4-[5-(1-methyl-5-trifluoromethyl-3-pyrazolyl)-2-thienylsulphonyl)piperazin-1-yl}[4-(5-methyl[1,2,4]-oxadiazol-3-yl)phenyl]methanone;
with 2,5-dichlorophenylsulphonyl chloride gives
[4-(2,5-dichlorophenylsulphonyl)piperazin-1-yl][4-(5-methyl[1,2,4]oxadiazol-3-yl)phenyl]methanone;
with 2,4,6-trimethylphenylsulphonyl chloride gives
[4-(2,4,6-trimethylphenylsulphonyl)piperazin-1-yl][4-(5-methyl[1,2,4]oxadiazol-3-yl)phenyl]methanone;
with 2-methylsulphonylphenylsulphonyl chloride gives
[4-(2-methylsulphonylphenylsulphonyl)piperazin-1-yl][4-(5-methyl[1,2,4]oxadiazol-3-yl)phenyl]methanone;
with 5-benzamidomethyl-2-thienylsulphonyl chloride gives
[4-(5-benzamidomethyl-2-thienylsulphonyl)piperazin-1-yl][4-(5-methyl[1,2,4]oxadiazol-3-yl)phenyl]methanone;
with methylsulphonyl chloride gives
[4-(methylsulphonyl)piperazin-1-yl][4-(5-methyl[1,2,4]oxadiazol-3-yl)phenyl]methanone;
with 1,3-dimethyl-5-chloro-4-pyrazolylsulphonyl chloride gives
[4-(1,3-dimethyl-5-chloro-4-pyrazolylsulphonyl)piperazin-1-yl][4-(5-methyl[1,2,4]oxadiazol-3-yl)phenyl]methanone;
with 3,5-dimethyl-4-isoxazolylsulphonyl chloride gives
[4-(3,5-dimethyl-4-isoxazolylsulphonyl)piperazin-1-yl][4-(5-methyl[1,2,4]oxadiazol-3-yl)phenyl]methanone;
with 4-bromo-2-ethylphenylsulphonyl chloride gives
[4-(4-bromo-2-ethylphenylsulphonyl)piperazin-1-yl][4-(5-methyl[1,2,4]oxadiazol-3-yl)phenyl]methanone;
with 1-naphthylsulphonyl chloride gives
[4-(1-naphthylsulphonyl)piperazin-1-yl][4-(5-methyl[1,2,4]oxadiazol-3-yl)phenyl]methanone;
with 5-dimethylamino-1-naphthylsulphonyl chloride gives
[4-(5-dimethylamino-1-naphthylsulphonyl)piperazin-1-yl][4-(5-methyl[1,2,4]oxadiazol-3-yl)phenyl]methanone;
with 3,4-difluorophenylsulphonyl chloride gives
[4-(3,4-difluorophenylsulphonyl)piperazin-1-yl][4-(5-methyl[1,2,4]oxadiazol-3-yl)phenyl]methanone;
with 4-tert-butylphenylsulphonyl chloride gives
[4-(4-tert-butylphenylsulphonyl)piperazin-1-yl][4-(5-methyl[1,2,4]oxadiazol-3-yl)phenyl]methanone;
with 4-ethylphenylsulphonyl chloride gives
[4-(4-ethylphenylsulphonyl)piperazin-1-yl][4-(5-methyl[1,2,4]oxadiazol-3-yl)phenyl]methanone;
with 4-(1,1-dimethylpropyl)phenylsulphonyl chloride gives
[4-(4-(1,1-dimethylpropyl)phenylsulphonyl)piperazin-1-yl][4-(5-methyl[1,2,4]oxadiazol-3-yl)phenyl]methanone;
with 4-isopropylphenylsulphonyl chloride gives
[4-(4-isopropylphenylsulphonyl)piperazin-1-yl][4-(5-methyl[1,2,4]oxadiazol-3-yl)phenyl]methanone;
with 4-trifluoromethylphenylsulphonyl chloride gives
[4-(4-trifluoromethylphenylsulphonyl)piperazin-1-yl][4-(5-methyl[1,2,4]oxadiazol-3-yl)phenyl]methanone;
with 3-nitro-4-methylphenylsulphonyl chloride gives
[4-(3-nitro-4-methylphenylsulphonyl)piperazin-1-yl][4-(5-methyl[1,2,4]oxadiazol-3-yl)phenyl]methanone;
with 4-pentylphenylsulphonyl chloride gives
[4-(4-pentylphenylsulphonyl)piperazin-1-yl][4-(5-methyl[1,2,4]oxadiazol-3-yl)phenyl]methanone;
with 4-butylphenylsulphonyl chloride gives
[4-(4-butylphenylsulphonyl)piperazin-1-yl][4-(5-methyl[1,2,4]oxadiazol-3-yl)phenyl]methanone;
with 3-chloro-4-methylphenylsulphonyl chloride gives
[4-(3-chloro-4-methylphenylsulphonyl)piperazin-1-yl][4-(5-methyl[1,2,4]oxadiazol-3-yl)phenyl]methanone.

EXAMPLE 2

A solution of 100 mg of [4-(6-chloronaphthalene-2-sulphonyl)piperazin-1-yl][4-(5-methyl[1,2,4]oxadiazol-3-yl)phenyl]methanone in 5 ml of methanol is admixed with 100 mg of Raney nickel and a drop of acetic acid and hydrogenated to completion at atmospheric pressure and room temperature. Catalyst and solvent are removed, giving 4-[4-(6-chloronaphthalene-2-sulphonyl)piperazin-1-carbonyl]benzamidine, acetate, FAB 457.

Similarly, the compounds below are obtained from the methanone derivatives listed under Example 1
4-[4-(4-biphenylylsulphonyl)piperazin-1-carbonyl] benzamidine, acetate, FAB 449;
4-[4-(2-naphthylsulphonyl)piperazin-1-carbonyl]-benzamidine, acetate, EI 405 ($M^+$–$NH_2$);
4-[4-(4-propylphenylsulphonyl)piperazin-1-carbonyl] benzamidine, acetate, FAB 415;
4-[4-(2-phenylvinylsulphonyl)piperazin-1-carbonyl] benzamidine, acetate, FAB 399;
4-[4-(3-amino-4-chlorophenylsulphonyl)piperazin-1-carbonyl]benzamidine, acetate, FAB 422;
4-(4-(2-amino-4-methoxyphenylsulphonyl)piperazin-1-carbonyl]benzamidine, acetate, FAB 418;
4-[4-(4-tolylsulphonyl)piperazin-1-carbonyl]benzamidine, acetate, FAB 387;
4-[4-(decylsulphonyl)piperazin-1-carbonyl]benzamidine, acetate, FAB 437;
4-[4-(benzylsulphonyl)piperazin-1-carbonyl]benzamidine, acetate, FAB 387;
4-[4-(3-amino-6-methylbenzylsulphonyl)piperazin-1-carbonyl]benzamidine, acetate, FAB 402;
4-[4-(2,3-dichlorophenylsulphonyl)piperazin-1-carbonyl] benzamidine, acetate, FAB 441;
4-[4-(3,4-dichlorophenylsulphonyl)piperazin-1-carbonyl] benzamidine, acetate, FAB 441;
4-[4-(phenylsulphonyl)piperazin-1-carbonyl]benzamidine, acetate, FAB 373;
4-[4-(3-bromophenylsulphonyl)piperazin-1-carbonyl] benzamidine, acetate, FAB 451, 453;
4-[4-(3,4-dimethoxyphenylsulphonyl)piperazin-1-carbonyl] benzamidine, acetate, FAB 433;
4-[4-(4-acetamido-3-chlorophenylsulphonyl)piperazin-1-carbonyl]benzamidine, acetate, FAB 464;
4-[4-(4-chloro-2,5-dimethylphenylsulphonyl)piperazin-1-carbonyl]benzamidine, acetate, FAB 435;
4-[4-(3-tolylsulphonyl)piperazin-1-carbonyl]-benzamidine, acetate, FAB 387;
4-[4-(2-methoxy-5-methylphenylsulphonyl)piperazin-1-carbonyl]benzamidine, acetate, FAB 417;
4-[4-(3-chlorophenylsulphonyl)piperazin-1-carbonyl] benzamidine, acetate, FAB 407;
4-[4-(4-methoxyphenylsulphonyl)piperazin-1-carbonyl] benzamidine, acetate, FAB 402;
4-[4-(2-thienylsulphonyl)piperazin-1-carbonyl]-benzamidine, acetate, FAB 379;

4-[4-(4-chlorophenylsulphonyl)piperazin-1-carbonyl]
benzamidine, acetate, FAB 407;
4-[4-(isopropylsulphonyl)piperazin-1-carbonyl]-
benzamidine, acetate, FAB 339;
4-[4-(1,2,3,4-tetrahydroquinolin-8-ylsulphonyl)piperazin-1-
carbonyl]benzamidine, acetate, FAB 428;
4-[4-(4-aminophenylsulphonyl)piperazin-1-carbonyl]
benzamidine, acetate, FAB 388;
4-[4-(3-chloro-6-methoxyphenylsulphonyl)piperazin-1-
carbonyl]benzamidine, acetate, FAB 437;
4-[4-(4-acetamidophenylsulphonyl)piperazin-1-carbonyl]
benzamidine, acetate, FAB 437;
4-[4-(2,2,5,7,8-pentamethylchroman-6-ylsulphonyl)
piperazin-1-carbonyl]benzamidine, acetate, FAB 499;
4-[4-(camphor-10-ylsulphonyl)piperazin-1-carbonyl]
benzamidine, acetate, FAB 447;
4-{4-([5-(1-methyl-5-trifluoromethyl-3-pyrazolyl)-2-
thienylsulphonyl]piperazin-1-carbonyl}benzamidine,
acetate, FAB 527;
4-[4-(2,5-dichlorophenylsulphonyl)piperazin-1-carbonyl]
benzamidine, acetate, FAB 441;
4-[4-(2,4,6-trimethylphenylsulphonyl)piperazin-1-
carbonyl]benzamidine, acetate, FAB 415;
4-[4-(2-methylsulphonylphenylsulphonyl)piperazin-1-
carbonyl]benzamidine, acetate, FAB 451;
4-[4-(5-benzamidomethyl-2-thienylsulphonyl)piperazin-1-
carbonyl]benzamidine, acetate, FAB 512;
4-[4-(methylsulphonyl)piperazin-1-carbonyl]-benzamidine,
acetate, EI 292 ($M^+-NH_2$);
4-[4-(1,3-dimethyl-5-chloro-4-pyrazolylsulphonyl)
piperazin-1-carbonyl]benzamidine, acetate;
4-[4-(3,5-dimethyl-4-isoxazolylsulphonyl)piperazin-1-
carbonyl]benzamidine, acetate;
4-[4-(4-bromo-2-ethylphenylsulphonyl)piperazin-1-
carbonyl]benzamidine, acetate, EI 461, 463 ($M^+-NH_2$);
4-[4-(1-naphthylsulphonyl)piperazin-1-carbonyl]
benzamidine, acetate, EI 405 ($M^+-NH_2$);
4-[4-(5-dimethylamino-1-naphthylsulphonyl)piperazin-1-
carbonyl]benzamidine, acetate, EI 448 ($M^+-NH_2$);
4-[4-(3,4-difluorophenylsulphonyl)piperazin-1-carbonyl]
benzamidine, acetate;
4-[4-(4-tert-butylphenylsulphonyl)piperazin-1-carbonyl]
benzamidine, acetate, FAB 429;
4-[4-(4-ethylphenylsulphonyl)piperazin-1-carbonyl]
benzamidine, acetate, FAB 401;
4-[4-(4-(1,1-dimethylpropyl)phenylsulphonyl)piperazin-1-
carbonyl]benzamidine, acetate, FAB 442;
4-[4-(4-isopropylphenylsulphonyl)piperazin-1-carbonyl]
benzamidine, acetate, FAB 415;
4-[4-(4-trifluoromethylphenylsulphonyl)piperazin-1-
carbonyl]benzamidine, acetate, FAB 441;
4-[4-(3-amino-4-methylphenylsulphonyl)piperazin-1-
carbonyl]benzamidine, acetate, FAB 402;
4-[4-(4-pentylphenylsulphonyl)piperazin-1-carbonyl]
benzamidine, acetate, FAB 443;
4-[4-(4-butylphenylsulphonyl)piperazin-1-carbonyl]
benzamidine, acetate, FAB 429;
4-(4-(3-chloro-4-methylphenylsulphonyl)piperazin-1-
carbonyl]benzamidine, acetate, FAB 421.

EXAMPLE 3

By reaction with equimolar amounts of methyl chloroformate in pyridine and catalytic amounts of dimethylaminopyridine, 4-[4-(6-chloronaphthalene-2-sulphonyl)piperazine-1-carbonyl]benzamidine gives, after customary work-up, the compound methyl {imino-[4-(4-(6-chloronaphthalene-2-sulphonyl)piperazine-1-carbonyl)phenyl]methyl}-carbamate.

EXAMPLE 4

Similarly to Example 1, reaction of 3-[4-(5-methyl[1,2,4]oxadiazol-3-yl)phenyl]-1-piperazin-1-ylpropan-1-one [obtainable from 3-[4-(5-methyl-[1,2,4]oxadiazol-3-yl)phenyl]-1-(4-tert-butyloxycarbonyl)piperazin-1-yl-propan-1-one by treatment with $TFA/CH_2Cl_2$] and 6-chloronaphthalene-2-sulphonyl chloride gives the compound 1-[4-(6-chloronaphthalene-2-sulphonyl)piperazin-1-yl]-3-[4-(5-methyl-[1,2,4]oxadiazol-3-yl)phenyl]propan-1-one and, after hydrogenation, 4-{3-oxo-3-[4-(6-chloronaphthalene-2-sulphonyl)piperazin-1-yl]propyl}benzamidine.

EXAMPLE 5

Similarly to Examples 1 and 2, reaction of [3-(5-methyl-[1,2,4]oxadiazol-3-yl)phenyl3piperazin-1-yl-methanone and 5-chloronaphthalene-2-sulphonyl chloride, followed by hydrogenation, gives the compound 3-[4-(6-chloronaphthalene-2-sulphonyl)piperazine-1-carbonyl]benzamidine, acetate, FAB 457.

Similarly, reaction of [3-(5-methyl-[1,2,4]oxadiazol-3-yl)phenyl]piperazin-1-ylmethanone with 4-propyl-phenylsulphonyl chloride and subsequent hydrogenation gives the compound 3-[4-(4-propylphenylsulphonyl)piperazine-1-carbonyl]benzamidine, acetate, FAB 415.

EXAMPLE 6

Similarly to Example 1, reaction of 2-[4-(5-methyl-[1,2,4]oxadiazol-3-yl)phenyl]-1-piperazin-1-ylethan-1-one ("B") and 4-propylphenylsulphonyl chloride gives the compound 1-[4-(4-propylphenylsulphonyl)piperazin-1-yl]-2-[4-(5-methyl-[1,2,4]oxadiazol-3-yl)phenyl]ethan-1-one and, after hydrogenation, 4-{2-oxo-2-[4-(4-propylphenylsulphonyl)piperazin-1-yl]ethyl}benzamidine, FAB 429.

Similarly, reaction of "B"
with decylsulphonyl chloride gives
1-[4-(decylsulphonyl)piperazin-1-yl]-2-[4-(5-methyl-[1,2,4]oxadiazol-3-yl)phenyl]ethan-1-one;
with phenylsulphonyl chloride gives
1-[4-(phenylsulphonyl)piperazin-1-yl]-2-[4-(5-methyl-[1,2,4]oxadiazol-3-yl)phenyl]ethan-1-one;
with 3,4-dichlorophenylsulphonyl chloride gives
1-[4-(3,4-dichlorophenylsulphonyl)piperazin-1-yl]-2-[4-(5-methyl-[1,2,4]oxadiazol-3-yl)phenyl]ethan-1-one;
with benzylsulphonyl chloride gives
1-[4-(benzylsulphonyl)piperazin-1-yl]-2-[4-(5-methyl-[1,2,4]oxadiazol-3-yl)phenyl]ethan-1-one;
with 3,4-dimethoxyphenylsulphonyl chloride gives
1-[4-(3,4-dimethoxyphenylsulphonyl)piperazin-1-yl]-2-[4-(5-methyl-[1,2,4]oxadiazol-3-yl)phenyl]ethan-1-one;
with isopropylsulphonyl chloride gives
1-(4-(isopropylsulphonyl)piperazin-1-yl]-2-[4-(5-methyl-[1,2,4]oxadiazol-3-yl)phenyl]ethan-1-one;
with camphor-10-ylsulphonyl chloride gives
1-[4-(camphor-10-ylsulphonyl)piperazin-1-yl]-2-[4-(5-methyl-[1,2,4]oxadiazol-3-yl)phenyl]ethan-1-one;
with 3-methoxy-4-methoxycarbonyl-2-thienylsulphonyl chloride gives
1-[4-(3-methoxy-4-methoxycarbonyl-2-thienyl-sulphonyl)piperazin-1-yl]-2-[4-(5-methyl-(1,2,4]-oxadiazol-3-yl)phenyl]ethan-1-one;
with 2,4,6-trimethylphenylsulphonyl chloride gives
1-[4-(2,4,6-trimethylphenylsulphonyl)piperazin-1-yl]-2-[4-(5-methyl-[1,2,4]oxadiazol-3-yl)phenyl]ethan-1-one;

with 2-phenylvinylsulphonyl chloride gives
1-[4-(2-phenylvinylsulphonyl)piperazin-1-yl]-2-[4-(5-methyl-[1,2,4]oxadiazol-3-yl)phenyl]ethan-1-one;
with methylsulphonyl chloride gives
1-[4-(methylsulphonyl)piperazin-1-2-[4-(5-methyl-[1,2,4]oxadiazol-3-yl)phenyl]ethan-1-one;
with [2,1,3]benzothiadiazol-4-ylsulphonyl chloride gives
1-[4-([2,1,3]benzothiadiazol-4-ylsulphonyl)piperazin-1-yl]-2-[4-(5-methyl-[1,2,4]oxadiazol-3-yl)phenyl]ethan-1-one;
with 2,4-dichlorophenylsulphonyl chloride gives
1-[4-(2,4-dichlorophenylsulphonyl)piperazin-1-yl]-2-[4-(5-methyl-[1,2,4]oxadiazol-3-yl)phenyl]ethan-1-one;
with 1-naphthylsulphonyl chloride gives
1-[4-(1-naphzhylsulphonyl)piperazin-1-yl]-2-[4-(5-methyl-[1,2,4]oxadiazol-3-yl)phenyl]ethan-1-one;
with 2-naphthylsulphonyl chloride gives
1-[4-(2-naphthylsulphonyl)piperazin-1-yl]-2-[4-(5-methyl-[1,2,4]oxadiazol-3-yl)phenyl]ethan-1-one;
with 5-dimethylamino-1-naphthylsulphonyl chloride gives
1-[4-(5-dimethylamino-1-naphthylsulphonyl)piperazin-1-yl]-2-[4-(5-methyl-[1,2,4]oxadiazol-3-yl)phenyl]ethan-1-one;
with 4-methylsulphonylphenylsulphonyl chloride gives
1-[4-(4-methylsulphonylphenylsulphonyl)piperazin-1-yl]-2-[4-(5-methyl-[1,2,4]oxadiazol-3-yl)phenyl]ethan-1-one.

By hydrogenation, these compounds yield the amidine derivatives below:
4-(2-oxo-2-[4-(decylsulphonyl)piperazin-1-yl]ethyl}benzamidine, acetate, FAB 450;
4-{2-oxo-2-[4-(phenylsulphonyl)piperazin-1-yl]-ethyl}benzamidine, acetate, FAB 387;
4-{2-oxo-2-[4-(3,4-dichlorophenylsulphonyl)piperazin-1-yl]ethyl}benzamidine, acetate, FAB 454;
4-{2-oxo-2-[4-(benzylsulphonyl)piperazin-1-yl]-ethyl}benzamidine, acetate, FAB 401;
4-{2-oxo-2-[4-(3,4-dimethoxyphenylsulphonyl)piperazin-1-yl)ethyl}benzamidine, acetate, FAB 447;
4-{2-oxo-2-[4-(isopropylsulphonyl)piperazin-1-yl]-ethyl}benzamidine, acetate, FAB 353;
4-(2-oxo-2-[4-(camphor-10-ylsulphonyl)piperazin-1-yl] ethyl}benzamidine, acetate, FAB 353;
4-{(2-oxo-2-[4-(3-methoxy-4-methoxycarbonyl-2-thienylsulphonyl)piperazin-1-yl]ethyl}benzamidine, acetate, FAB 481;
4-{2-oxo-2-[4-(2,4,6-trimethylphenylsulphonyl)piperazin-1-yl]ethyl}benzamidine, acetate, FAB 429;
4-{2-oxo-2-[4-(2-phenylvinylsulphonyl)piperazin-1-yl] ethyl}benzamidine, acetate, FAB 413;
4-{2-oxo-2-[4-(methylsulphonyl)piperazin-1-yl] ethyl}benzamidine, acetate, FAB 325;
4-{2-oxo-2-[4-(2,3-diaminophenylsulphonyl)piperazin-1-yl]ethyl}benzamidine, acetate, FAB 415;
4-{2-oxo-2-[4-(2,4-dichlorophenylsulphonyl)piperazin-1-yl]ethyl}benzamidine, acetate, FAB 455;
4-{2-oxo-2-[4-(!-naphthylsulphonyl)piperazin-1-yl] ethyl}benzamidine, acetate, FAB 437;
4-{2-oxo-2-[4-(2-naphthylsulphonyl)piperazin-1-yl] ethyl}benzamidine, acetate, FAB 437;
4-{2-oxo-2-[4-(5-dimethylamino-1-naphthyl-sulphonyl) piperazin-1-yl]ethyl}benzamidine, acetate, FAB 480;
4-{2-oxo-2-[4-(4-methylsulphonylphenylsulphonyl) piperazin-1-yl]ethyl}benzamidine, acetate, FAB 465.

EXAMPLE 7

Similarly to Example 1, reaction of "A"
with 4-biphenylylcarbonyl chloride gives
[4-(4-phenylbenzoyl)piperazin-1-yl][4-(5-methyl-[1,2,4] oxadiazol-3-yl)phenyl]methanone;
with cyclopentylcarbonyl chloride gives
[4-(cyclopentylcarbonyl)piperazin-1-yl][4-(5-methyl-[1,2,4]oxadiazol-3-yl)phenyl]methanone;
with phenoxyacetyl chloride gives
[4-(phenoxyacetyl)piperazin-1-yl][4-(5-methyl-[1,2,4] oxadiazol-3-yl)phenyl]methanone;
with 1-naphthylcarbonyl chloride gives
[4-(1-naphthylcarbonyl)piperazin-1-yl][4-(5-methyl-[1,2,4] oxadiazol-3-yl)phenyl]methanone;
with 2-naphthylcarbonyl chloride gives
[4-(2-naphthylcarbonyl)piperazin-1-yl][4-(5-methyl-[1,2,4] oxadiazol-3-yl)phenyl]methanone;
with nicotinoyl chloride gives
[4-(nicotinoyl)piperazin-1-yl][4-(5-methyl-[1,2,4] oxadiazol-3-yl)phenyl]methanone;
with 3-nitrobenzoyl chloride gives
[4-(3-nitrobenzoyl)piperazin-1-yl][4-(5-methyl-[1,2,4] oxadiazol-3-yl)phenyl]methanone;
with benzo-[b]thiophene-2-carbonyl chloride gives
[4-(benzo-[b]thiophene-2-carbonyl)piperazin-1-yl][4-(5-methyl-[1,2,4]oxadiazol-3-yl)phenyl]methanone;
with 4-trifluoromethoxybenzoyl chloride gives
[4-(4-trifluoromethoxybenzoyl)piperazin-1-yl][4-(5-methyl-[1,2,4]oxadiazol-3-yl)phenyl]methanone;
with 2,5-dimethoxyphenylacetyl chloride gives
[4-(2,5-dimethoxyphenylacetyl)piperazin-1-yl][4-(5-methyl-[1,2,4]oxadiazol-3-yl)phenyl]methanone;
with 4-chlorophenylacetyl chloride gives
[4-(4-chlorophenylacetyl)piperazin-1-yl][4-(5-methyl-[1,2,4]oxadiazol-3-yl)phenyl]methanone;
with 1,3-benzodioxol-5-carbonyl chloride gives
[4-(1,3-benzodioxol-5-carbonyl)piperazin-1-yl][4-(5-methyl-[1,2,4]oxadiazol-3-yl)phenyl]methanone;
with 3,4-dichlorobenzoyl chloride gives
[4-(3,4-dichlorobenzoyl)piperazin-1-yl][4-(5-methyl-[1,2,4]oxadiazol-3-yl)phenyl]methanone;
with isobutyl chloroformate gives
[4-(isobutyloxycarbonyl)piperazin-1-yl][4-(5-methyl-[1,2,4]oxadiazol-3-yl)phenyl]methanone.

By hydrogenation, these compounds yield the amidine derivatives below:
4-[4-(4-phenylbenzoyl)piperazine-1-carbonyl]benzamidine, acetate, FAB 413;
4-[4-(cyclopentylcarbonyl)piperazine-1-carbonyl] benzamidine, acetate, FAB 329;
4-[4-(phenoxyacetyl)piperazine-1-carbonyl]benzamidine, acetate, FAB 367;
4-[4-(1-naphthylcarbonyl)piperazine-1-carbonyl] benzamidine, acetate, FAB 387;
4-[4-(2-naphthylcarbonyl)piperazine-1-carbonyl] benzamidine, acetate, FAB 387;
4-[4-(nicotinoyl)piperazine-1-carbonyl]benzamidine, acetate, FAB 338;
4-[4-(3-aminobenzoyl)piperazine-1-carbonyl]benzamidine;
4-[4-(benzo-[b]thiophene-2-carbonyl)piperazine-1-carbonyl]benzamidine, acetate, FAB 393;
4-[4-(4-trifluoromethoxybenzoyl)piperazine-1-carbonyl] benzamidine, acetate, FAB 421;
4-[4-(2,5-dimethoxyphenylacetyl)piperazine-1-carbonyl] benzamidine, acetate, FAB 411;
4-[4-(4-chlorophenylacetyl)piperazine-1-carbonyl] benzamidine, acetate, FAB 385;

4-[4-(1,3-benzodioxol-5-carbonyl)piperazine-1-carbonyl]
benzamidine, acetate, FAB 381;
4-[4-(3,4-dichlorobenzoyl)piperazine-1-carbonyl]
benzamidine, acetate, FAB 381;
4-[4-(isobutyloxycarbonyl)piperazine-1-carbonyl]
benzamidine, acetate, FAB 333.

EXAMPLE 8

Reaction of equimolar amounts of acetyl chloride in pyridine and catalytic amounts of dimethylaminopyridine gives, after customary work-up
with 4-[4-(6-chloronaphthalene-2-sulphonyl)piperazine-1-carbonyl]benzamidine
N-{imino-4-[4-(6-chloronaphthalene-2-sulphonyl)piperazine-1-carbonyl]phenylmethyl}acetamide.

EXAMPLE 9

Reaction of equimolar amounts of 4-cyanobenzyl bromide, BOC-piperazine and triethylamine in dichloromethane gives 1-(4-cyanobenzyl)-4-(tert-butyloxycarbonyl)piperazine. Reaction with
   a) hydroxylamine hydrochloride, triethylamine in ethanol and
   b) acetic anhydride gives 1-[4-(5-methyl-[1,2,4] oxadiazol-3-yl)benzyl]-4-(tert-butyloxycarbonyl) piperazine.

Similarly to Examples 1 and 2, after removal of the BOC group with TFA in CH$_2$Cl$_2$, reaction of 1-[4-(5-methyl-[1, 2,4]oxadiazol-3-yl)benzyl]piperazine with 6-chloronaphthalene-2-sulphonyl chloride, subsequent hydrogenation and customary work-up gives the compound 4-[(6-chloronaphthalene-2-sulphonyl)piperazin-1-ylmethyl] benzamidine.

The compounds below are obtained similarly:
4-[(4-biphenylylsulphonyl)piperazin-1-yl-methyl] benzamidine,
4-[(2-naphthylsulphonyl)piperazin-1-yl-methyl] benzamidine,
4-[(4-propylphenylsulphonyl)piperazin-1-yl-methyl] benzamidine and
4-[(2-phenylvinylsulphonyl)piperazin-1-yl-methyl] benzamidine.

EXAMPLE 10

Reaction of equimolar amounts of 4-(5-methyl-[1,2,4] oxadiazol-3-yl]benzoic acid, diphenylphosphoryl azide and triethylamine in DMF gives, after customary work-up, 4-(5-methyl-[1,2,4]oxadiazol-3-yl)benzoyl azide.

Heating with BOC-piperazine in toluene gives in a rearrangement reaction, after customary work-up, 1-BOC-4-[4-(5-methyl-[1,2,4]oxadiazol-3-yl)phenylcarbamoyl]-piperazine. Removal of the BOC group with TFA in CH$_2$C$_2$ gives 4-[4-(5-methyl-[1,2,4]oxadiazol-3-yl)phenyl-carbamoyl]piperazine ("C").

Similarly to Examples 1 and 2, reaction of "C" with 6-chloronaphthalenesulphonyl chloride and subsequent hydrogenation gives the compound N-(4-amidinophenyl)-4-(6-chloronaphthalene-2-sulphonyl)piperazine-1-carboxamide.

The compounds below are obtained similarly
N-(4-amidinophenyl)-4-(4-biphenylylsulphonyl)-piperazine-1-carboxamide,
N-(4-amidinophenyl)-4-(2-naphthylsulphonyl)-piperazine-1-carboxamide,
N-(4-amidinophenyl)-4-(4-propylphenylsulphonyl)-piperazine-1-carboxamide and
N-(4-amidinophenyl)-4-(2-phenylvinylsulphonyl)-piperazine-1-carboxamide.

EXAMPLE 11

Reaction of equimolar amounts of 1-BOC-4-[4-(5-methyl-[1,2,4]oxadiazol-3-yl)phenylcarbamoyl]piperazine, methyl bromoacetate and potassium tert-butoxide in DMF gives, after customary work-up, the compound methyl {(4-BOC-piperazine-1-carbonyl)[4-(5-methyl-[1,2,4]oxadiazol-3-yl)phenyl]amino}acetate. Reaction with
   a) HCl/dioxane and b) NaOH gives the compound methyl {(piperazine-1-carbonyl)[4-(5-methyl-[1,2,4] oxadiazol-3-yl)phenyl]amino}acetate.

Reaction with 6-chloronaphthalenesulphonyl chloride gives, similarly to Example 1, the compound methyl {[4-(6-chloronaphthalene-2-sulphonyl)piperazine-1-carbonyl] (4-(5-methyl-[1,2,4]oxadiazol-3-yl)phenyl]amino}acetate.

This gives, by hydrogenation over Raney nickel, methyl {[4-(6-chloronaphthalene-2-sulphonyl)piperazine-1-carbonyl][4-amidinophenyl]amino}acetate.

The methyl ester is cleaved by treatment with NaOH in methanol/water. Customary work-up affords ([4-(6chloronaphthalene-2-sulphonyl)piperazine-1-carbonyl](4-amidinophenyl]amino}acetic acid.

Similarly, the compounds below are obtained
{[4-(4-biphenylylsulphonyl)piperazine-1-carbonyl]-(4-amidinophenyl]amino}acetic acid,
{[4-(2-naphthylsulphonyl)piperazine-1-carbonyl][4-amidinophenyl]amino}acetic acid,
{[4-(4-propylphenylsulphonyl)piperazine-1-carbonyl][4-amidinophenyl]amino}acetic acid and
{[4-(2-phenylvinylsulphonyl)piperazine-1-carbonyl][4-amidinophenyl]amino}acetic acid.

EXAMPLE 12

Reaction of equimolar amounts of 4-(5-methyl-[1,2,4] oxadiazol-3-yl)phenylacetic acid, methyl iodide and potassium carbonate gives methyl 4-(5-methyl-[1,2,4]oxadiazol-3-yl)phenylacetate ("D").

Heating of equimolar amounts of BOC-piperazine and chloroacetyl chloride in toluene gives, after customary work-up, 1-BOC-4-chloromethylcarbonylpiperazine ("E"). Reaction of "D" and "E" with NaH in DMF gives, after customary work-up, the compound methyl 4-(4-BOC-piperazin-1-yl)-2-[4-(5-methyl-[1,2,4]oxadiazol-3-yl)-phenyl]-4-oxobutyrate Reaction with
   a) HCl/dioxane and b) NaOH gives the compound methyl 4-(piperazin-1-yl)-2-[4-(5-methyl-[1,2,4]oxadiazol-3-yl)phenyl]-4-oxobutyrate.

Reaction with 6-chloronaphthalenesulphonyl chloride gives, similarly to Example 1, the compound methyl 4-[4-(6-chloronaphthalene-2-sulphonyl)piperazin-1-yl]-2-[4-(5-methyl-[1,2,4]oxadiazol-3-yl)phenyl]-4-oxobutyrate.

This gives, by hydrogenation similar to Example 2, the compound methyl 4-[4-(6-chloronaphthalene-2-sulphonyl)-piperazin-1-yl]-2-[4-amidinophenyl]-4-oxobutyrate.

The methyl ester is cleaved by treatment with NaOH in methanol/water. Customary work-up gives 4-[4-(6-chloronaphthalene-2-sulphonyl)piperazin-1-yl]-2-(4-amidinophenyl)-4-oxobutyric acid.

The compounds below are obtained in a similar manner
4-[4-(4-biphenylylsulphonyl)piperazin-1-yl]-2-(4-amidinophenyl)-4-oxobutyric acid,
4-[4-(2-naphthylsulphonyl)piperazin-1-yl]-2-(4-amidinophenyl)-4-oxobutyric acid, 4-[4-(4-propylphenylsulphonyl)piperazin-1-yl]-2-(4-amidinophenyl)-4-oxobutyric acid and
4-[4-(2-phenylvinylsulphonyl)piperazin-1-yl]-2-(4-amidinophenyl)-4-oxobutyric acid.

EXAMPLE 13

Reaction of equimolar amounts of "A" and phenyl isocyanate in dichloromethane at room temperature gives, after customary work-up, the compound N-phenyl-4-[4-(5-methyl-[1,2,4]oxadiazol-3-yl)benzoyl]-piperazine-1-carboxamide.

Similarly, reaction of "A"
with 4-trifluoromethylphenyl isocyanate gives
N-(4-trifluoromethylphenyl)-4-[4-(5-methyl-[1,2,4]oxadiazol-3-yl)benzoyl]piperazine-1-carboxamide;
with butyl isocyanate gives
N-butyl-4-[4-(5-methyl-[1,2,4]oxadiazol-3-yl)benzoyl]piperazine-1-carboxamide;
with 1-naphthyl isocyanate gives
N-(1-naphthyl)-4-[4-(5-methyl-[1,2,4]oxadiazol-3-yl)benzoyl]piperazine-1-carboxamide;
with 4-methoxyphenyl isocyanate gives
N-(4-methoxyphenyl)-4-[4-(5-methyl-[1,2,4]oxadiazol-3-yl)benzoyl]piperazine-1-carboxamide;
with 4-nitrophenyl isocyanate gives
N-(4-nitrophenyl)-4-[4-(5-methyl-[1,2,4]oxadiazol-3-yl)benzoyl]piperazine-1-carboxamide;
with cyclohexyl isocyanate gives
N-cyclohexyl-4-[4-(5-methyl-[1,2,4]oxadiazol-3-yl)benzoyl]piperazine-1-carboxamide;
with 3-ethoxycarbonylphenyl isocyanate gives
N-(3-ethoxycarbonylphenyl)-4-[4-(5-methyl-[1,2,4]oxadiazol-3-yl)benzoyl]piperazine-1-carboxamide.

These compounds give, by hydrogenation similarly to Example 2, the amidine derivatives below
N-phenyl-4-(4-amidinobenzoyl)piperazine-1-carboxamide, acetate, FAB 352;
N-butyl-4-(4-amidinobenzoyl)piperazine-1-carboxamide, acetate, FAB 332;
N-(1-naphthyl)-4-(4-amidinobenzoyl)piperazine-1-carboxamide, acetate, FAB 402;
N-(4-methoxyphenyl)-4-(4-amidinobenzoyl)piperazine-1-carboxamide, acetate, FAB 382;
N-(4-aminophenyl)-4-(4-amidinobenzoyl)piperazine-1-carboxamide, acetate, FAB 367;
N-cyclohexyl-4-(4-amidinobenzoyl)piperazine-1-carboxamide, acetate, FAB 358;
N-(3-ethoxycarbonylphenyl)-4-(4-amidinobenzoyl)piperazine-1-carboxamide, acetate, FAB 424.

EXAMPLE 14

Similarly to Examples 1 and 2, the compounds below are obtained
3-[4-(2-naphthylsulphonyl)piperazine-1-carbonyl]benzamidine, acetate, FAB 423;
3-[4-(3-chloro-4-methylphenylsulphonyl)piperazine-1-carbonyl]benzamidine, acetate, FAB 421;
3-[4-(2,4,6-trichlorophenylsulphonyl)piperazine-1-carbonyl]benzamidine, acetate, FAB 475, 477;
3-[4-(3-amino-4-chlorophenylsulphonyl)piperazine-1-carbonyl]benzamidine, acetate, FAB 422;
3-[4-(4-chlorophenylsulphonyl)piperazine-1-carbonyl]benzamidine, acetate, FAB 407;
3-[4-(3-trifluoromethylphenylsulphonyl)piperazine-1-carbonyl]benzamidine, acetate, FAB 441;
3-[4-(4-biphenylylsulphonyl)piperazine-1-carbonyl]benzamidine, acetate, FAB 449;
4-[4-(3,5-dimethoxyphenylsulphonyl)piperazine-1-carbonyl]benzamidine, acetate, FAB 433;
4-[4-(dibenzofuran-2-ylsulphonyl)piperazine-1-carbonyl]benzamidine, acetate, FAB 463;
4-[4-(3-fluoro-4-methoxyphenylsulphonyl)-piperazine-1-carbonyl]benzamidine, acetate, FAB 421;
4-[4-(2,4-dichloro-6-methoxyphenylsulphonyl)piperazine-1-carbonyl]benzamidine, acetate, FAB 471;
4-(4-benzylpiperazine-1-carbonyl)benzamidine, acetate, FAB 323;
4-[4-(2-naphthylmethyl)piperazine-1-carbonyl]benzamidine, acetate, FAB 373;
4-[4-(4-methoxyphenylmethyl)piperazine-1-carbonyl]benzamidine, diacetate, FAB 353;
4-[4-(4-methoxycarbonylphenylsulphonyl)-piperazine-1-carbonyl]benzamidine, acetate, FAB 431;
4-[4-(4-propylphenylsulphonyl)piperazine-1-carbonyl]-3-methylbenzamidine, acetate, FAB 429;
4-[4-(2-naphzhylsulphonyl)piperazine-1-carbonyl]3-methylbenzamidine, acetate, FAB 437;
4-[4-(6-chloro-2-naphthylsulphonyl)piperazine-1-carbonyl]-3-methylbenzamidine, acetate, FAB 471;
4-[4-(7-methoxy-2-naphthylsulphonyl)piperazine-1-carbonylbenzamidine, acetate, FAB 453;
4-[4-(3,5-dimethoxyphenylmethyl)piperazine-1-carbonyl]benzamidine, acetate, FAB 383;

EXAMPLE 15

Similarly to Example 6, the compounds below are obtained
4-{3-oxo-3-[4-(butylsulphonyl)piperazin-1-yl]-propyl}benzamidine, acetate, FAB 381;
4-{3-oxo-3-[4-(4-propylphenylsulphonyl)piperazin-1-yl]propyl}benzamidine, acetate, FAB 443;
4-{3-oxo-3-[4-(6-chloro-2-naphthylsulphonyl)piperazin-1-yl]propyl}benzamidine, acetate, FAB 485;
4-{3-oxo-3-[4-(2-naphthylsulphonyl)piperazin-1-yl]propyl}benzamidine, acetate, FAB 451;
4-{3-oxo-3-[4-(3-chloro-4-methylphenylsulphonyl)-piperazin-1-yl]propyl}benzamidine, acetate, FAB 449;
4-{3-oxo-3-[4-(4-chlorophenylsulphonyl)piperazin-1-yl]propyl}benzamidine, acetate, FAB 435;
4-{3-oxo-3-[4-(4-biphenylylsulphonyl)piperazin-1-yl]propyl}benzamidin, acetate, FAB 477;
4-{3-oxo-3-[4-(2-4,6-trimethylphenylsulphonyl)-piperazin-1-yl]propyl}benzamidine, acetate, FAB 443;
3-{3-oxo-3-[4-(butylsulphonyl)piperazin-1-yl)-propyl}benzamidine, acetate, FAB 381;
3-{3-oxo-3-(4-(4-methoxyphenylsulphonyl)piperazin-1-yl]propyl}benzamidine, acetate, FAB 431;
3-{3-oxo-3-[4-(4-chlorophenylsulphonyl)piperazin-1-yl]propyl}benzamidine, acetate, FAB 435;
3-{3-oxo-3-[4-(4-isopropylphenylsulphonyl)piperazin-1-yl]propyl}benzamidine, acetate, FAB 443;
3-{3-oxo-3-[4-(2,4,06-trimethylphenylsulphonyl)piperazin-1-yl]propyl}benzamidine, acetate, FAB 443;
3-{3-oxo-3-[4-(3-chloro-4-methylphenylsulphonyl)piperazin-1-yl]propyl}benzamidine, acetate, FAB 449;
3-{3-oxo-3-[4-(6-chloro-2-naphthylsulphonyl)piperazin-1-yl]propyl}benzamidine, acetate, FAB 485;
3-{3-oxo-3-[4-(2-naphthylsulphonyl)piperazin-1-yl]propyl}benzamidine, acetate, FAB 451;
3-{3-oxo-3-[4-(4-biphenylylsulphonyl)piperazin-1-yl]propyl}benzamidine, acetate, FAB 477;

EXAMPLE 16

Similarly to Example 13, reaction or 4-(5-methyl-[1,2,4]oxadiazol-3-yl)phenyl isocyanate ("F")
with 1-(2-naphthylsulphonyl)piperazine gives
N-[4-(5-methyl-[1,2,4]oxadiazol-3-yl)phenyl]-4-(2-naphthylsulphonyl)piperazine-1-carboxamide

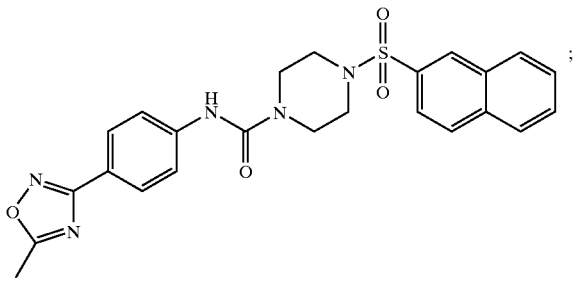

with 1-(2-phenylvinylsulphonyl)piperazine gives
N-[4-(5-methyl-[1,2,4]oxadiazol-3-yl)phenyl]-4-(2-phenylvinylsulphonyl)piperazine-1-carboxamide;
with 1-(4-propylphenylsulphonyl)piperazine gives
N-[4-(5-methyl-[1,2,4]oxadiazol-3-yl)phenyl]-4-(4-propylphenylsulphonyl)piperazine-1-carboxamide;
with 1-(4-chlorophenylsulphonyl)piperazine gives
N-[4-(5-methyl-[1,2,4]oxadiazol-3-yl)phenyl]-4-(4-chlorophenylsulphonyl)piperazine-1-carboxamide;
with 1-(2,4,6-trimethylphenylsulphonyl)piperazine gives
N-[4-(5-methyl-[1,2,4]oxadiazol-3-yl)phenyl]-4-(2,4,6-trimethylphenylsulphonyl)piperazine-1-carboxamide;
with 1-(6-chloro-2-naphthylsulphonyl)piperazine gives
N-[4-(5-methyl-[1,2,4]oxadiazol-3-yl)phenyl]-4-(6-chloro-2-naphthylsulphonyl)piperazine-1-carboxamide.

By hydrogenation similarly to example 2, these give the amidine derivatives below
N-(4-amidinophenyl)-4-(2-naphthylsulphonyl)piperazine-1-carboxamide, acetate, FAB 438;
N-(4-amidinophenyl)-4-(2-phenylvinylsulphonyl)piperazine-1-carboxamide, acetate, FAB 414;
N-(4-amidinophenyl)-4-(4-propylphenylsulphonyl)-piperazine-1-carboxamide, acetate, FAB 430;
N-(4-amidinophenyl)-4-(4-chlorophenylsulphonyl)-piperazine-1-carboxamide, acetate, FAB 422;
N-(4-amidinophenyl)-4-(2,4,6-trimethylphenylsulphonyl)piperazine-1-carboxamide, acetate, FAB 430;
N-(4-amidinophenyl)-4-(6-chloro-2-naphthylsulphonyl)piperazine-1-carboxamide, acetate, FAB 472.

EXAMPLE 17

Similarly to Example 1, reaction of 1-[4-(5-methyl-[1,2,4]oxadiazol-3-yl)benzyl]piperazine ("G")
with 4-propylphenylsulphonyl chloride gives
1-[4-(5-methyl-[1,2,4]oxadiazol-3-yl)benzyl]-4-(4-propylphenylsulphonyl)piperazine;
with 4-methoxyphenylsulphonyl chloride gives
1-[4-(5-methyl-[1,2,4]oxadiazol-3-yl)benzyl]-4-(4-methoxyphenylsulphonyl) piperazine;
with 4-biphenylylsulphonyl chloride gives
1-[4-(5-methyl- [1,2,4]oxadiazol-3-yl)benzyl]-4-(4-biphenylylsulphonyl)piperazine;
with 2-naphthylsulphonyl chloride gives
1-[4-(5-methyl-[1,2,4]oxadiazol-3-yl)benzyl]-4-(2-naphzhylsulphonyl)piperazine;
with 6-chloro-2-naphthylsulphonyl chloride gives
1-[4-(5-methyl-[1,2,4]oxadiazol-3-yl)benzyl]-4-(6-chloro-2-naphthylsulphonyl)piperazine;
with 7-methoxy-2-naphthylsulphonyl chloride gives
1-[4-(5-methyl-[1,2,4]oxadiazol-3-yl)benzyl]-4-(7-methoxy-2-naphthylsulphonyl)piperazine;
with 3,5-dimethoxybenzyl chloride gives
1-[4-(5-methyl-[1,2,4]oxadiazol-3-yl)benzyl]-4-(3,5-dimethoxybenzyl)piperazine;
with 4-isopropylphenylsulphonyl chloride gives
1-[4-(5-methyl-[1,2,4]oxadiazol-3-yl)benzyl]-4-(4-isopropylphenylsulphonyl)piperazine;
with 4-biphenylylcarbonyl chloride gives
1-[4-(5-methyl-[1,2,4]oxadiazol-3-yl)benzyl]-4-(4-biphenylylcarbonyl)piperazine;
with 2-naphthylcarbonyl chloride gives
1-[4-(5-methyl-[1,2,4]oxadiazol-3-yl)benzyl]-4-(2-naphthylcarbonyl)piperazine;
with 3,5-dimethoxybenzyl chloride gives
1-[4-(5-methyl-[1,2,4]oxadiazol-3-yl)benzyl]-4-(3,5-dimethoxybenzyl)piperazine;
with 2-naphthylmethyl chloride gives
1-[4-(5-methyl-[1,2,4]oxadiazol-3-yl)benzyl]-4-(2-naphthylmethyl)piperazine.

By hydrogenation similarly to Example 2, these give the amidine derivatives below.
1-(4-amidinobenzyl)-4-(4-propylphenylsulphonyl) piperazine, acetate, FAB 401;
1-(4-amidinobenzyl)-4-(4-methoxyphenylsulphonyl) piperazine, acetate, FAB 389;
1-(4-amidinobenzyl)-4-(4-biphenylylsulphonyl)piperazine, acetate, FAB 435;
1-(4-amidinobenzyl)-4-(2-naphthylsulphonyl)piperazine, acetate, FAB 409;
1-(4amidinobenzyl)-4-(6-chloro-2-naphthylsulphonyl) piperazine, acetate, FAB 443;
1-(4-amidinobenzyl)-4-(7-methoxy-2-naphthylsulphonyl) piperazine, acetate, FAB 439;
1-(4-amidinobenzyl)-4-(3,5-dimethoxybenzyl)piperazine, acetate, FAB 369;
1-(4-amidinobenzyl)-4-(4-isopropylphenylsulphonyl) piperazine, acetate, FAB 441;
1-(4-amidinobenzyl)-4-(4-biphenylylcarbonyl)piperazine, diacetate, FAB 399;
1-(4-amidinobenzyl)-4-(2-naphthylcarbonyl)piperazine, diacetate, FAB 373;
1-(4-amidinobenzyl)-4-(3,5-dimethoxybenzyl)piperazine, diacetate, FAB 369;
1-(4-amidinobenzyl)-4-(2-naphthylmethyl)piperazine, diacetate, FAB 359.

EXAMPLE 18

By reaction of 4-[4-(6-chloro-2-naphthylsulphonyl) piperazine-1-carbonyl]-3-methylbenzamidine with methyl chloroformate in dichloromethane, the compound methyl (imino-{4-[4- (6-chloro-2-naphthylsulphonyl)piperazine-1-carbonyl]phenyl}methyl)carbamate is obtained after customary work-up

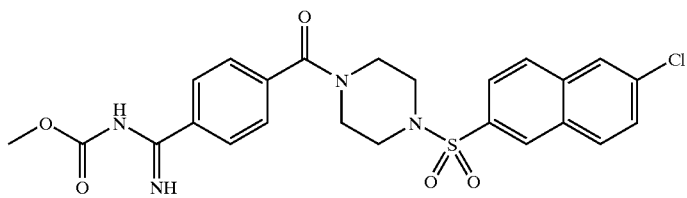

, FAB 515.

EXAMPLE 19

Similarly to Example 1, reaction of 1-[4-(5-methyl-[1,2,4]oxadiazol-3-yl)phenyl]-piperazine
with 4-propylphenylsulphonyl chloride gives
1-[4-(5-methyl-[1,2,4]oxadiazol-3-yl)phenyl]-4-(4-propylphenylsulphonyl)piperazine;
with 4-butylsulphonyl chloride gives
1-[4-(5-methyl-[1,2,4]oxadiazol-3-yl)phenyl]-4-(4-butylsulphonyl)piperazine;
with 4-methoxyphenylsulphonyl chloride gives
1-[4-(5-methyl-[1,2,4]oxadiazol-3-yl)phenyl]-4-(4-methoxyphenylsulphonyl)piperazine;
with 4-chlorophenylsulphonyl chloride gives
1-[4-(5-methyl-[1,2,4]oxadiazol-3-yl)phenyl]-4-(4-chlorophenylsulphonyl)piperazine;
with 4-isopropylphenylsulphonyl chloride gives
1-[4-(5-methyl-[1,2,4]oxadiazol-3-yl)phenyl]-4-(4-isopropylphenylsulphonyl)piperazine;
with 4-biphenylylsulphonyl chloride gives
1-[4-(5-methyl-[1,2,4]oxadiazol-3-yl)phenyl]-4-(4-biphenylylphenylsulphonyl)piperazine;
with 2,4,6-trimethylphenylsulphonyl chloride dives
1-[4-(5-methyl-[1,2,4]oxadiazol-3-yl)phenyl]-4-(2,4,6-trimethylphenylsulphonyl)piperazine;
with 3-chloro-4-methylphenylsulphonyl chloride gives
1-[4-(5-methyl-[1,2,4]oxadiazol-3-yl)phenyl]-4-(3-chloro-4-methylphenylsulphonyl)piperazine;
with 2-naphthylsulphonyl chloride gives
1-[4-(5-methyl-[1,2,4]oxadiazol-3-yl)phenyl]-4-(2-naphthylsulphonyl)piperazine;
with 6-chloro-2-naphzhylsulphonyl chloride gives
1-[4-(5-methyl-[1,2,4]oxadiazol-3-yl)phenyl]-4-(6-chloro-2-naphthylsulphonyl)piperazine By hydrogenation similarly to Example 2, these give the amidine derivatives below
1-(4-amidinophenyl)-4-(4-propylphenylsulphonyl) piperazine, acetate, FAB 387;
1-(4-amidinophenyl)-4-(4-butylsulphonyl)-piperazine, acetate, FAB 325;
1-(4-amidinophenyl)-4-(4-methoxyphenylsulphonyl) piperazine, acetate, FAB 375;
1-(4-amidinophenyl)-4-(4-chlorophenylsulphonyl) piperazine, acetate, FAB 379;
1-(4-amidinophenyl)-4-(4-isopropylphenylsulphonyl) piperazine, acetate, FAB 387;
1-(4-amidinophenyl)-4-(4-biphenylylphenylsulphonyl) piperazine, acetate, FAB 421;
1-(4-amidinophenyl)-4-(2,4,6-trimethylphenyl-sulphonyl) piperazine, acetate, FAB 387;
1-(4-amidinophenyl)-4-(3-chloro-4-methylphenyl-sulphonyl)piperazine, acetate, FAB 393;
1-(4-amidinophenyl)-4-(2-naphthylsulphonyl)-piperazine, acetate, FAB 395;
1-(4-amidinophenyl)-4-(6-chloro-2-naphthyl-sulphonyl) piperazine, acetate, FAB 429.

The following examples relate to pharmaceutical formulations:

Example A

Injection Vials

A solution of 100 g of an active compound of the formula I and 5 g of disodium hydrogen phosphate in 3 l of doubly distilled water is brought to pH 6.5 with 2 N hydrochloric acid and subjected to sterile filtration, and injection vials are filled with the solution, lyophilized under sterile conditions and closed under sterile conditions. Each injection vial contains 5 mg of active compound.

Example B

Suppositories

A mixture of 20 g of an active compound of the formula I with 100 g of soya lecithin and 1400 g of cocoa butter is melted, poured into moulds and allowed to cool. Each suppository contains 20 mg of active compound.

Example C

Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of doubly distilled water. It is brought to pH 6.8, topped up to 1 l and sterilized by irradiation. This solution can be used in the form of eyedrops.

Example D

Ointment 500 g of an active compound of the formula I are mixed wish 99.5 g of vaseline under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed into tablets in the customary manner such that each tablet contains 10 mg of active compound.

Example F

Coated Tablets

Tablets are pressed analogously to Example E and are then coated in the customary manner with a coating of sucrose, potato starch, talc, tragacanth gum and dyestuff.

Example G

Capsules

Hard gelatin capsules are filled with 2 kg of active compound of the formula I in the customary manner such that each capsule contains 20 mg of the active compound.

Example H

Ampoules

A solution of 1 kg of active compound of the formula I in 60 l of doubly distilled water is subjected to sterile filtration, and ampoules are filled with the solution, lyophilized under sterile conditions and closed under sterile conditions. Each ampoule contains 10 mg of active compound.

What is claimed is:

1. A compound of formula I

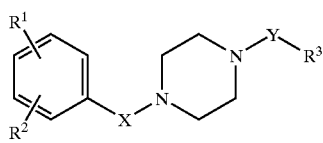

in which $R^1$ is —C(=NH)—$NH_2$ which is optionally monosubstituted by —COA, —CO—[C($R^6$)$_2$]$_n$—Ar, or —COOA, or $R^1$ is

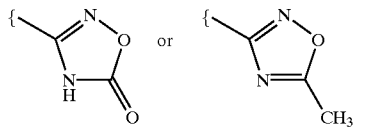

$R^2$ is H, A, $OR^6$, N($R^6$)$_2$, $NO_2$, CN, Hal, NHCOA, NHCOAr, $NHSO_2$A, $NHSO_2$Ar, $COOR^6$, CON($R^6$)$_2$, CONHAr, $COR^6$, COAr, S(O)$_n$A or S(O)$_n$Ar, $R^3$ is A, cycloalkyl, —[C($R^6$)$_2$]$_n$Ar, or —[C($R^6$)$_2$]$_n$—O—Ar, $R^6$ is H, A or benzyl, X is absent, —C($R^6$)$_2$—, —C($R^6$)$_2$—C($R^6$)$_2$—, —C($R^6$)$_2$—CO—, —C($R^6$)$_2$—C($R^6$)$_2$—CO—, —C($R^6$)$_2$=C($R^6$)—CO—, —$NR^6$CO—, —N{[C($R^6$)$_2$]$_n$—$COOR^6$}—CO— or —C($COOR^6$)$R^6$—C($R^6$)$_2$—CO—, Y is —C($R^6$)$_2$—, —$SO_2$—, —CO—, or —COO—, A is alkyl having 1–20 C atoms in which one or two $CH_2$ groups are optionally replaced in each case by O or S atoms or by —$CR^6$=$CR^6$— groups, and 1–7 H atoms are optionally replaced by F, Ar is naphthyl or phenyl which is unsubstituted or mono-, di- or trisubstituted by A, Ar', $OR^6$, N($R^6$)$_2$, $NO_2$, CN, Hal, NHCOA, NHCOAr', $NHSO_2$A, $NHSO_2$Ar', $COOR^6$, CON($R^6$)$_2$, CONHAr', $COR^6$, COAr', S(O)$_n$A or S(O)$_n$Ar, Ar' is naphthyl or phenyl which is unsubstituted or mono-, di- or trisubstituted by A, $OR^6$, N($R^6$)$_2$, $NO_2$, CN, Hal, NHCOA, $COOR^6$, CON($R^6$)$_2$, $COR^6$ or S(O)$_n$A, Hal is F, Cl, Br or I, n is 0, 1 or 2, or a salt thereof.

2. A compound according to claim 1, wherein $R^1$ is —C(=NH)—$NH_2$, or —C(=NH)—$NH_2$ which is monosubstituted by —COA, —CO—[C($R^6$)$_2$]$_n$—Ar, or —COOA.

3. A compound according to claim 1, wherein $R^2$ is H, fluorine, chlorine, bromine, iodine, hydroxyl, methoxy, ethoxy, propoxy, nitro, amino, methylamino, dimethylamino, ethylamino, diethylamino, acetamido, sulphonamido, methylsulphonamido, phenylsulphonamido, methylthio, ethylthio, methylsulphinyl, ethylsulphinyl, methylsulphonyl, ethylsulphonyl, phenylsulphinyl, phenylsulphonyl, cyano, carboxyl, methoxycarbonyl, ethoxycarbonyl or benzoyl.

4. A compound according to claim 1, wherein $R^6$ is H, A or benzyl.

5. A compound according to claim 1, wherein X is absent or is —$CH_2$—, —$CH_2$—$CH_2$—, —$CH_2$—CO—, —$CH_2$—$CH_2$—CO—, —CH=CH—CO—, —$NR^6$CO—, —N{[$CH_2$]$_n$—$COOR^6$}—CO— or —CH($COOR^6$)—$CH_2$—CO—.

6. A compound according to claim 1, wherein Y is —$SO_2$—, —CO—, —COO—, or —$CH_2$—.

7. A compound according to claim 1, wherein $R^3$ is A, cycloalkyl, Ar, $CH_2$Ar, $CH_2$OAr, or $CH_2CH_2$Ar, $R^6$ is H or A, X is absent or is —$CH_2$—CO—, —$CH_2$—$CH_2$—CO—, —$CH_2$—, —$CH_2$—$CH_2$—, —CH=CH—CO—, —NHCO—, —N($CH_2COOR^6$)—CO— or —CH($COOR^6$)—$CH_2$—CO—, and Y is —$SO_2$—, —CO—, —COO—, or —$CH_2$.

8. A compound according to claim 1, wherein $R^2$ is H, $R^3$ is A, cycloalkyl, Ar, $CH_2$Ar, $CH_2$OAr, or —$CH_2CH_2$Ar, $R^6$ is H or A, X is —$CH_2$—CO—, —$CH_2$—$CH_2$—CO—, —$CH_2$—, —$CH_2$—$CH_2$—, —CH=CH—CO—, —NHCO—, —N($CH_2COOR^6$)—CO— or —CH($COOR^6$)—$CH_2$—CO—, Y is —$SO_2$—, —CO—, —COO—, or —$CH_2$—, Ar is naphthyl or phenyl which is unsubstituted or mono-, di- or trisubstituted by A, Ar', $OR^6$, $NH_2$, $NO_2$, CN, Hal, NHCOA, NHCOAr', $NHSO_2$A, $NHSO_2$Ar', $COOR^6$, CON($R^6$)$_2$, CONHAr', $COR^6$, COAr', S(O)$_n$A or S(O)$_n$Ar, and Ar' is naphthyl or phenyl which is unsubstituted or mono-, di- or trisubstituted by A, $OR^6$, N($R^6$)$_2$, $NO_2$, CN, Hal, NHCOA, $COOR^6$, CON($R^6$)$_2$, $COR^6$ or S(O)$_n$A.

9. A compound according to claim 1, wherein R1 is 5-methyl-[1,2,4-oxadiazol-3-yl].

10. A compound according to claim 1, wherein Y is —$SO_2$—.

11. A process for preparing a pharmaceutical formulation comprising: combining a compound of formula I according to claim 1 or one of its physiologically acceptable salts into a suitable dosage form together with at least one solid, liquid or semi-liquid carrier or auxiliary.

12. A pharmaceutical composition comprising at least one compound of formula I according to claim 1 or one of its physiologically acceptable salts, and at least one solid, liquid or semi-liquid carrier or auxiliary.

13. A method for treating a patient suffering from thromboses, myocardial infarction, arteriosclerosis, inflammations, apoplexy, angina pectoris, restenosis after angioplasty or claudicatio intermittens, comprising administering to said patient an effective amount of a compound of formula I according to claim 1 or a physiologically acceptable salt thereof.

14. A compound of formula I

[Structure I: R¹ and R² on phenyl ring connected via X to piperazine, other nitrogen connected to Y—R³]

wherein
R¹ is —C(=NH)—NH₂, which is optionally monosubstituted by —COA, —CO—[C(R⁶)₂]ₙ—Ar, —COOA, or by an amino-protective group, or R¹ is

[Two heterocyclic structures: oxadiazolone NH and oxadiazole with CH₃]

R² is H,
R³ is A, cycloalkyl, Ar, —CH₂Ar, —CH₂OAr, —CH₂CH₂Ar, —CH₂Het, —CH₂CH₂Het or —CH=CH—Ar,
R⁶ is H or A,
X is —CH₂—CO—, —CH₂—CH₂—CO—, —CH₂—, —CH₂—CH₂—, —CH=CH—CO—, —NHCO—, —N{CH₂COOR⁶}—CO— or —CH(COOR⁶)—CH₂—CO—,
Y is —SO₂—, —CO—, —COO—, —CO—NH— or —CH₂—,
A is alkyl having 1–20 C atoms in which one or two CH₂ groups are optionally replaced in each case by O or S atoms or by —CR⁶=CR⁶— groups, and 1–7 H atoms are optionally replaced by F,
Ar is naphthyl or phenyl which is unsubstituted or mono-, di- or trisubstituted by A, Ar', OR⁶, N(R⁶)₂, NO₂, CN, Hal, NHCOA, NHCOAr', NHSO₂A, NHSO₂Ar', COOR⁶, CON(R⁶)₂, CONHAr', COR⁶, COAr', S(O)ₙA or S(O)ₙAr,
Ar' is naphthyl or phenyl which is unsubstituted or mono-, di- or trisubstituted by A, OR⁶, N(R⁶)₂, NO₂, CN, Hal, NHCOA, COOR⁶, CON(R⁶)₂, COR⁶ or S(O)ₙA,
Het is thiophene, tetrahydroquinoline, chroman, pyrazole, isoxazole, pyridine, benzodioxole or benzothiophene, which in each case is unsubstituted or mono- or polysubstituted by Hal, A, Ar', COOR⁶, CN, N(R⁶)₂, NO₂, Ar—CONH—CH₂ and/or carbonyl oxygen,
Hal is F, Cl, Br or I, and
n is 0, 1 or 2; or
a salt thereof.

15. A compound of formula I

[Structure I]

wherein
R¹ is —C(=NH)—NH₂, which is optionally monosubstituted by —COA, —CO—[C(R⁶)₂]ₙ—Ar, —COOA, or by an amino-protective group, or R¹ is

[Two heterocyclic structures: oxadiazolone NH and oxadiazole with CH₃]

R² is H,
R³ is A, cycloalkyl, Ar, —CH₂Ar, —CH₂OAr, —CH₂CH₂Ar, —CH₂Het, —CH₂CH₂Het or —CH=CH—Ar,
R⁶ is H or A,
X is —CH₂—CO—, —CH₂—CH₂—CO—, —CH₂—, —CH₂—CH₂—, —CH=CH—CO—, —NHCO—, —N{CH₂COOR⁶}—CO— or —CH(COOR⁶)—CH₂—CO—,
Y is —SO₂—, —CO—, or —CO—NH—,
A is alkyl having 1–20 C atoms in which one or two CH₂ groups are optionally replaced by O or S atoms or by —CR⁶=CR⁶— groups, and 1–7 H atoms are optionally replaced by F,
Ar is naphthyl or phenyl which is unsubstituted or mono-, di- or trisubstituted by A, Ar', OR⁶, N(R⁶)₂, NO₂, CN, Hal, NHCOA, NHCOAr', NHSO₂A, NHSO₂Ar', COOR⁶, CON(R⁶)₂, CONHAr', COR⁶, COAr', S(O)ₙA or S(O)ₙAr,
Ar' is phenyl,
Het is thiophene, tetrahydroquinoline, chroman, pyrazole, isoxazole, pyridine, benzodioxole, benzothiophene or dibenzofuran, which in each case is unsubstituted or mono- or polysubstituted by Hal, A, Ar', COOR⁶, CN, N(R⁶)₂, NO₂, Ar—CONH—CH₂ and/or carbonyl oxygen,
Hal is F, Cl, Br or I, and
n is 0, 1 or 2; or
a salt thereof.

16. A compound according to claim 15, wherein
X is —CH₂—CO—, —CH₂—CH₂—CO—, —CH₂—, —CH₂—CH₂—, —NHCO—, —N{CH₂COOR⁶}—CO— or —CH(COOR⁶)—CH₂—CO—.

17. A compound of formula I

[Structure I]

wherein
R¹ is —C(=NH)—NH₂, which is optionally monosubstituted by COOA,

[Two heterocyclic structures: oxadiazolone NH and oxadiazole with CH₃]

R² is H,
R³ is A, cycloalkyl, Ar, —CH₂Ar, —CH₂OAr, —CH₂CH₂Ar, —CH₂Het, —CH₂CH₂Het or —CH=CH—Ar,
R⁶ is H or A, X is absent or is —CH$_2$—CO—, —CH$_2$—CH$_2$—CO—, —CH$_2$—, —CH$_2$—CH$_2$—, —NHCO—, —N{CH$_2$COOR$^6$}—CO— or —CH(COOR$^6$)—CH$_2$—CO—, Y is —SO$_2$—, —CO—, or —CH$_2$—, A is alkyl having 1–20 C atoms in which one or two CH$_2$ groups are optionally replaced in each case by O or S atoms or by —CR$^6$═CR$^6$— groups, and 1–7 H atoms are optionally replaced by F, Ar is naphthyl or phenyl which is unsubstituted or mono-, di- or trisubstituted by A, Ar', OR$^6$, N(R$^6$)$_2$, NO$_2$, CN, Hal, NHCOA, NHCOAr', NHSO$_2$A, NHSO$_2$Ar', COOR$^6$, CON(R$^6$)$_2$, CONHAr', COR$^6$, COAr', S(O)$_n$A or S(O)$_n$Ar, Ar' is phenyl, Het is thiophene, tetrahydroquinoline, chroman, pyrazole, isoxazole, pyridine, benzodioxole, benzothiophene or dibenzofuran, which in each case is unsubstituted or mono- or polysubstituted by Hal, A, Ar', COOR$^6$, CN, N(R$^6$)$_2$, NO$_2$, Ar—CONH—CH$_2$ and/or carbonyl oxygen, Hal is F, Cl, Br or I, and n is 0, 1 or 2; or a salt thereof.

18. A compound according to claim 16, wherein Y is —SO$_2$—.

19. A compound of formula I

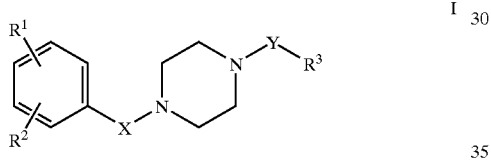

in which

R$^1$ is —C(═NH)—NH$_2$ which is optionally monosubstituted by —COA, —CO—[C(R$^6$)$_2$]$_n$—Ar, or —COOA, or R$^1$ is

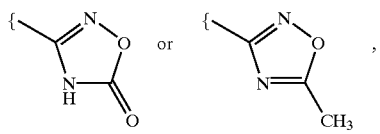

R$^2$ is H, A, OR$^6$, N(R$^6$)$_2$, NO$_2$, CN, Hal, NHCOA, NHCOAr, NHSO$_2$A, NHSO$_2$Ar, COOR$^6$, CON(R$^6$)$_2$, CONHAr, COR$^6$, COAr, S(O)$_n$A or S(O)$_n$Ar,

R$^3$ is A, cycloalkyl, —[C(R$^6$)$_2$]$_n$Ar, or —[C(R$^6$)$_2$]$_n$—O—Ar,

R$^6$ is H, A or benzyl,

X is —C(R$^6$)$_2$—, —C(R$^6$)$_2$—C(R$^6$)$_2$—, —C(R$^6$)$_2$—CO—, —C(R$^6$)$_2$—C(R$^6$)$_2$—CO—, —C(R$^6$)$_2$═C(R$^6$)—CO—, —NR$^6$CO—, —N{[C(R$^6$)$_2$]$_n$—COOR$^6$}—CO— or —C(COOR$^6$)R$^6$—C(R$^6$)$_2$—CO—,

Y is —C(R$^6$)$_2$—, —SO$_2$—, —CO—, —COO— or —CONR$^6$—,

A is alkyl having 1–20 C atoms in which one or two CH$_2$ groups are optionally replaced in each case by O or S atoms or by —CR$^6$═CR$^6$— groups, and 1–7 H atoms are optionally replaced by F, Ar is naphthyl or phenyl which is unsubstituted or mono-, di- or trisubstituted by A, Ar', OR$^6$, N(R$^6$)$_2$, NO$_2$, CN, Hal, NHCOA, NHCOAr', NHSO$_2$A, NHSO$_2$Ar', COOR$^6$, CON(R$^6$)$_2$, CONHAr', COR$^6$, COAr', S(O)$_n$A or S(O)$_n$Ar, Ar' is naphthyl or phenyl which is unsubstituted or mono-, di- or trisubstituted by A, OR$^6$, N(R$^6$)$_2$, NO$_2$, CN, Hal, NHCOA, COOR$^6$, CON(R$^6$)$_2$, COR$^6$ or S(O)$_n$A, Hal is F, Cl, Br or I, n is 0, 1 or 2, or a salt thereof.

20. A compound of formula I

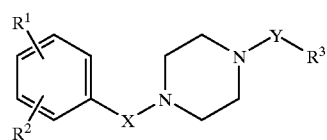

in which

R$^1$ is —C(═NH)—NH$_2$ which is optionally monosubstituted by —COA, —CO—[C(R$^6$)$_2$]$_n$—Ar, or —COOA, or R$^1$ is

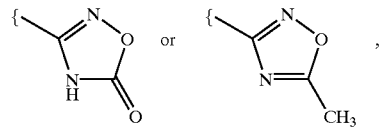

R$^2$ is H, A, OR$^6$, N(R$^6$)$_2$, NO$_2$, CN, Hal, NHCOA, NHCOAr, NHSO$_2$A, NHSO$_2$Ar, COOR$^6$, CON(R$^6$)$_2$, CONHAr, COR$^6$, COAr, S(O)$_n$A or S(O)$_n$Ar,

R$^3$ is A, cycloalkyl, —[C(R$^6$)$_2$]$_n$Ar, or —[C(R$^6$)$_2$]$_n$—O—Ar,

R$^6$ is H, A or benzyl,

X is absent, —C(R$^6$)$_2$—, —C(R$^6$)$_2$—, —C(R$^6$)$_2$—CO—, —C(R$^6$)$_2$—C(R$^6$)$_2$—CO—, —C(R$^6$)$_2$═C(R$^6$)—CO—, —NR$^6$CO—, —N{[C(R$^6$)$_2$]$_n$—COOR$^6$}—CO— or —C(COOR$^6$)R$^6$—C(R$^6$)$_2$—CO—, Y is —C(R$^6$)$_2$—, —SO$_2$—, —CO—, —COO— or —CONR$^6$—, A is alkyl having 1–20 C atoms in which one or two CH$_2$ groups are optionally replaced in each case by O or S atoms or by —CR$^6$═CR$^6$— groups, and 1–7 H atoms are optionally replaced by F, Ar is naphthyl or phenyl which is unsubstituted or mono-, di- or trisubstituted by A, Ar', N(R$^6$)$_2$, NO$_2$, CN, Hal, NHCOA, NHCOAr', NHSO$_2$A, NHSO$_2$Ar', COOR$^6$, CON(R$^6$)$_2$, CONHAr', COR$^6$, COAr', S(O)$_n$A or S(O)$_n$Ar, Ar' is naphthyl or phenyl which is unsubstituted or mono-, di- or trisubstituted by A, OR$^6$, N(R$^6$)$_2$, NO$_2$, CN, Hal, NHCOA, COOR$^6$, CON(R$^6$)$_2$, COR$^6$ or S(O)$_n$A, Hal is F, Cl, Br or I, n is 0, 1 or 2, or a salt thereof.

21. A compound of formula I

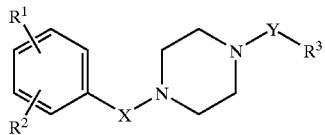

in which
R$^1$ is —C(=NH)—NH$_2$ which is optionally monosubstituted by —COA, —CO—[C(R$^6$)$_2$]$_n$—Ar, or —COOA, or R$^1$ is

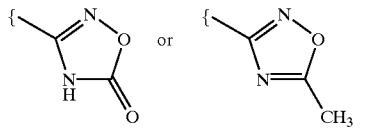

R$^2$ is H, A, OR$^6$, N(R$^6$)$_2$, NO$_2$, CN, Hal, NHCOA, NHCOAr, NHSO$_2$A, NHSO$_2$Ar, COOR$^6$, CON(R$^6$)$_2$, CONHAr, COR$^6$, COAr, S(O)$_n$A or S(O)$_n$Ar,

R$^3$ is A, cycloalkyl, —[C(R$^6$)$_2$]$_n$Ar, or —[C(R$^6$)$_2$]$_n$—O—Ar,

R$^6$ is H, A or benzyl,

X is absent, —CO—, —C(R$^6$)$_2$—, —C(R$^6$)$_2$—C(R$^6$)$_2$—, —C(R$^6$)$_2$—CO—, —C(R$^6$)$_2$—C(R$^6$)$_2$—CO—, —C(R$^6$)$_2$=C(R$^6$)—CO—, —NR$^6$CO—, —N{[C(R$^6$)$_2$]$_n$—COOR$^6$}—CO— or —C(COOR$^6$)R$^6$—C(R$^6$)$_2$—CO—, Y is —C(R$^6$)$_2$—, —CO—, or —COO—, A is alkyl having 1–20 C atoms in which one or two CH$_2$ groups are optionally replaced in each case by O or S atoms or by —CR$^6$=CR$^6$— groups, and 1–7 H atoms are optionally replaced by F, Ar is naphthyl or phenyl which is unsubstituted or mono-, di- or trisubstituted by A, Ar', OR$^6$, N(R$^6$)$_2$, NO$_2$, CN, Hal, NHCOA, NHCOAr', NHSO$_2$A, NHSO$_2$Ar', COOR$^6$, CON(R$^6$)$_2$, CONHAr', COR$^6$, COAr', S(O)$_n$A or S(O)$_n$Ar, Ar' is naphthyl or phenyl which is unsubstituted or mono-, di- or trisubstituted by A, OR$^6$, N(R$^6$)$_2$, NO$_2$, CN, Hal, NHCOA, COOR$^6$, CON(R$^6$)$_2$, COR$^6$ or S(O)$_n$A, Hal is F, Cl, Br or I, n is 0, 1 or 2, or a salt thereof.

22. A compound according to claim 21, wherein X is absent or is —CO—, —CH$_2$—, —CH$_2$—CH$_2$—, —CH$_2$—CO—, —CH$_2$—CH$_2$—CO—, —CH=CH—CO—, —NR$^6$CO—, —N{[CH$_2$]$_n$—COOR$^6$}—CO— or —CH(COOR$^6$)—CH$_2$—CO—.

23. A compound according to claim 21, wherein Y is —CO—, —COO—, or —CH$_2$—.

24. A compound according to claim 21, wherein
R$^3$ is A, cycloalkyl, Ar, CH$_2$Ar, CH$_2$OAr, or CH$_2$CH$_2$Ar,
R$^6$ is H or A,
X is absent or is —CO—, —CH$_2$—CO—, —CH$_2$—CH$_2$—CO—, —CH$_2$, —CH$_2$—CH$_2$—, —CH=CH—CO—, —NHCO—, —N(CH$_2$COOR$^6$)—CO— or —CH(COOR$^6$)—CH$_2$—CO—, and
Y is —CO—, —COO—, or —CH$_2$.

25. A compound according to claim 21, wherein
R$^2$ is H,
R$^3$ is A, cycloalkyl, Ar, CH$_2$Ar, CH$_2$OAr, or —CH$_2$CH$_2$Ar,
R$^6$ is H or A,
X is —CO—, —CH$_2$—CO—, —CH$_2$—CH$_2$—CO—, —CH$_2$—, —CH$_2$—CH$_2$—, —CH=CH—CO—, —NHCO—, —N(CH$_2$COOR$^6$)—CO— or —CH(COOR$^6$)—CH$_2$—CO—,
Y is —CO—, —COO—, or —CH$_2$—,
Ar is naphthyl or phenyl which is unsubstituted or mono-, di- or trisubstituted by A, Ar', OR$^6$, NH$_2$, NO$_2$, CN, Hal, NHCOA, NHCOAr', NHSO$_2$A, NHSO$_2$Ar', COOR$^6$, CON(R$^6$)$_2$, CONHAr', COR$^6$, COAr', S(O)$_n$A or S(O)$_n$Ar, and
Ar' is naphthyl or phenyl which is unsubstituted or mono-, di- or trisubstituted by A, OR$^6$, N(R$^6$)$_2$, NO$_2$, CN, Hal, NHCOA, COOR$^6$, CON(R$^6$)$_2$, COR$^6$ or S(O)$_n$A.

26. A compound of formula I

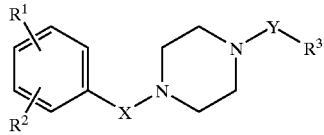

wherein
R$^1$ is —C(=NH)—NH$_2$, which is optionally monosubstituted by —COA, —CO—[C(R$^6$)$_2$]$_n$—Ar, —COOA, or by an amino-protective group, or R$^1$ is

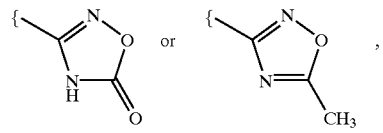

R$^2$ is H,
R$^3$ is A, cycloalkyl, Ar, —CH$_2$Ar, —CH$_2$OAr, —CH$_2$CH$_2$Ar, —CH$_2$Het, —CH$_2$CH$_2$Het or —CH=CH—Ar,
R$^6$ is H or A,
X is —CO—, —CH$_2$—CO—, —CH$_2$—CH$_2$—CO—, —CH$_2$—, —CH$_2$—CH$_2$—, —CH=CH—CO—, —NHCO—, —N{CH$_2$COOR$^6$}—CO— or —CH(COOR$^6$)—CH$_2$—CO—,
Y is —CO—, —COO—, —CO—NH— or —CH$_2$—,
A is alkyl having 1–20 C atoms in which one or two CH$_2$ groups are optionally replaced in each case by O or S atoms or by —CR$^6$=CR$^6$— groups, and 1–7 H atoms are optionally replaced by F,
Ar is naphthyl or phenyl which is unsubstituted or mono-, di- or trisubstituted by A, Ar', OR$^6$, N(R$^6$)$_2$, NO$_2$, CN, Hal, NHCOA, NHCOAr', NHSO$_2$A, NHSO$_2$Ar', COOR$^6$, CON(R$^6$)$_2$, CONHAr', COR$^6$, COAr', S(O)$_n$A or S(O)$_n$Ar,
Ar' is naphthyl or phenyl which is unsubstituted or mono-, di- or trisubstituted by A, OR$^6$, N(R$^6$)$_2$, NO$_2$, CN, Hal, NHCOA, COOR$^6$, CON(R$^6$)$_2$, COR$^6$ or S(O)$_n$A,
Het is thiophene, tetrahydroquinoline, chroman, pyrazole, isoxazole, pyridine, benzodioxole or benzothiophene, which in each case is unsubstituted or mono- or polysubstituted by Hal, A, Ar', COOR$^6$, CN, N(R$^6$)$_2$, NO$_2$, Ar—CONH—CH$_2$ and/or carbonyl oxygen, Hal is F, Cl, Br or I, and n is 0, 1 or 2; or a salt thereof.

27. A compound of formula I

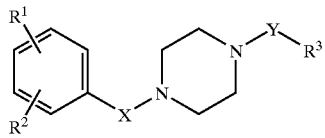

I wherein

R¹ is —C(=NH)—NH₂, which is optionally monosubstituted by —COA, —CO—[C(R⁶)₂]ₙ—Ar, —COOA, or by an amino-protective group, or R¹ is

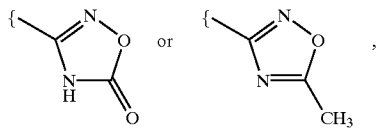

R² is H,

R³ is A, cycloalkyl, Ar, —CH₂Ar, —CH₂OAr, —CH₂CH₂Ar, —CH₂Het, —CH₂CH₂Het or —CH=CH—Ar, R⁶ is H or A, X is —CO—, —CH₂—CO—, —CH₂—CH₂—CO—, —CH₂—, —CH₂—CH₂—, —CH=CH—CO—, —NHCO—, —N{CH₂COOR⁶}—CO— or —CH(COOR⁶)—CH₂—CO—, Y is —CO— or —CO—NH—, A is alkyl having 1–20 C atoms in which one or two CH₂ groups are optionally replaced by O or S atoms or by —CR⁶=CR⁶— groups, and 1–7 H atoms are optionally replaced by F, Ar is naphthyl or phenyl which is unsubstituted or mono-, di- or trisubstituted by A, Ar', OR⁶, N(R⁶)₂, NO₂, CN, Hal, NHCOA, NHCOAr', NHSO₂A, NHSO₂Ar', COOR⁶, CON(R⁶)₂, CONHAr', COR⁶, COAr', S(O)ₙA or S(O)ₙAr, Ar' is phenyl, Het is thiophene, tetrahydroquinoline, chroman, pyrazole, isoxazole, pyridine, benzodioxole, benzothiophene or dibenzofuran, which in each case is unsubstituted or mono- or polysubstituted by Hal, A, Ar', COOR⁶, CN, N(R⁶)₂, NO₂, Ar—CONH—CH₂ and/or carbonyl oxygen, Hal is F, Cl, Br or I, and n is 0, 1 or 2; or a salt thereof.

28. A compound according to claim 27, wherein

X is —CO—, —CH₂—CO—, —CH₂—CH₂—CO—, —CH₂—, —CH₂—CH₂—, —NHCO—, —N{CH₂COOR⁶}—CO— or —CH(COOR⁶)—CH₂—CO—.

29. A compound of formula I

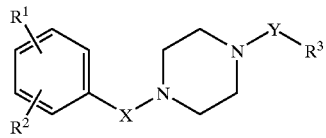

I wherein

R¹ is —C(=NH)—NH₂, which is optionally monosubstituted by COOA,

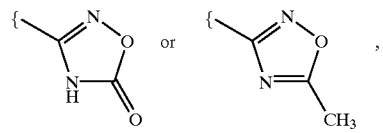

R² is H,

R³ is A, cycloalkyl, Ar, —CH₂Ar, —CH₂OAr, —CH₂CH₂Ar, —CH₂Het, —CH₂CH₂Het or —CH=CH—Ar, R⁶ is H or A, X is absent or is —CO—, —CH₂—CO—, —CH₂—CH₂—CO—, —CH₂, —CH₂—CH₂—, —NHCO—, —N{CH₂COOR⁶}—CO— or —CH(COOR⁶)—CH₂—CO—, Y is —CO— or —CH₂—, A is alkyl having 1–20 C atoms in which one or two CH₂ groups are optionally replaced in each case by O or S atoms or by —CR⁶=CR⁶— groups, and 1–7 H atoms are optionally replaced by F, Ar is naphthyl or phenyl which is unsubstituted or mono-, di- or trisubstituted by A, Ar', OR⁶, N(R⁶)₂, NO₂, CN, Hal, NHCOA, NHCOAr', NHSO₂A, NHSO₂Ar', COOR⁶, CON(R⁶)₂, CONHAr', COR⁶, COAr', S(O)ₙA or S(O)ₙAr, Ar' is phenyl, Het is thiophene, tetrahydroquinoline, chroman, pyrazole, isoxazole, pyridine, benzodioxole, benzothiophene or dibenzofuran, which in each case is unsubstituted or mono- or polysubstituted by Hal, A, Ar', COOR⁶, CN, N(R⁶)₂, NO₂, Ar—CONH—CH₂ and/or carbonyl oxygen, Hal is F, Cl, Br or I, and n is 0, 1 or 2; or a salt thereof.

30. A compound of formula I

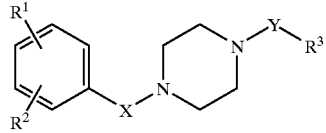

I in which

R¹ is —C(=NH)—NH₂ which is optionally monosubstituted by —COA, —CO—[C(R⁶)₂]ₙ—Ar, or —COOA, or R¹ is

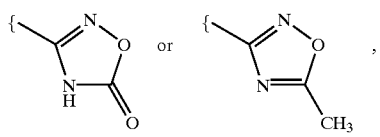 or , $R^2$ is H, A, $OR^6$, $N(R^6)_2$, $NO_2$, CN, Hal, NHCOA, NHCOAr, $NHSO_2A$, $NHSO_2Ar$, $COOR^6$, $CON(R^6)_2$, CONHAr, $COR^6$, COAr, $S(O)_nA$ or $S(O)_nAr$, $R^3$ is A, cycloalkyl, $-[C(R^6)_2]_n-Ar$, or $-[C(R^6)_2]_n-O-Ar$, $R^6$ is H, A or benzyl, X is $-CO-$, $-C(R^6)_2-$, $-C(R^6)_2-C(R^6)_2-$, $-C(R^6)_2-CO-$, $-C(R^6)_2-C(R^6)_2-CO-$, $-C(R^6)_2=C(R^6)-CO-$, $-NR^6CO-$, $-N\{[C(R^6)_2]_n-COOR^6\}-CO-$ or $-C(COOR^6)R^6-C(R^6)_2-CO-$, Y is $-C(R^6)_2-$, $-CO-$, $-COO-$ or $-CONR^6-$, A is alkyl having 1–20 C atoms in which one or two $CH_2$ groups are optionally replaced in each case by O or S atoms or by $-CR^6=CR^6-$ groups, and 1–7 H atoms are optionally replaced by F, Ar is naphthyl or phenyl which is unsubstituted or mono-, di- or trisubstituted by A, Ar', $OR^6$, $N(R^6)_2$, $NO_2$, CN, Hal, NHCOA, NHCOAr', $NHSO_2A$, $NHSO_2Ar'$, $COOR^6$, $CON(R^6)_2$, CONHAr', $COR^6$, COAr', $S(O)_nA$ or $S(O)_nAr$, Ar' is naphthyl or phenyl which is unsubstituted or mono-, di- or trisubstituted by A, $OR^6$, $N(R^6)_2$, $NO_2$, CN, Hal, NHCOA, $COOR^6$, $CON(R^6)_2$, $COR^6$ or $S(O)_nA$, Hal is F, Cl, Br or I, n is 0, 1 or 2, or a salt thereof.

31. A compound of formula I

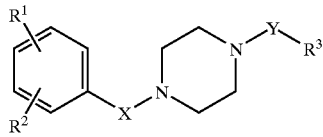

I in which $R^1$ is $-C(=NH)-NH_2$ which is optionally monosubstituted by $-COA$, $-CO-[C(R^6)_2]_n-Ar$, or $-COOA$, or $R^1$ is

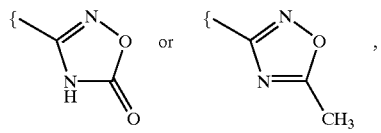 or , $R^2$ is H, A, $OR^6$, $N(R^6)_2$, $NO_2$, CN, Hal, NHCOA, NHCOAr, $NHSO_2A$, $NHSO_2Ar$, $COOR^6$, $CON(R^6)_2$, CONHAr, $COR^6$, COAr, $S(O)_nA$ or $S(O)_nAr$, $R^3$ is A, cycloalkyl, $-[C(R^6)_2]_n-Ar$, or $-[C(R^6)_2]_n-O-Ar$, $R^6$ is H, A or benzyl, X is absent, $-CO-$, $-C(R^6)_2-$, $-C(R^6)_2-C(R^6)_2-$, $-C(R^6)_2-CO-$, $-C(R^6)_2-C(R^6)_2-CO-$, $-C(R^6)_2=C(R^6)-CO-$, $-NR^6CO-$, $-N\{[C(R^6)_2]_n-COOR^6\}-CO-$ or $-C(COOR^6)R^6-C(R^6)_2-CO-$, Y is $-C(R^6)_2-$, $-CO-$, $-COO-$ or $-CONR^6-$, A is alkyl having 1–20 C atoms in which one or two $CH_2$ groups are optionally replaced in each case by O or S atoms or by $-CR^6=CR^6-$ groups, and 1–7 H atoms are optionally replaced by F, Ar is naphthyl or phenyl which is unsubstituted or mono-, di- or trisubstituted by A, Ar', $N(R^6)_2$, $NO_2$, CN, Hal, NHCOA, NHCOAr', $NHSO_2A$, $NHSO_2Ar'$, $COOR^6$, $CON(R^6)_2$, CONHAr', $COR^6$, COAr', $S(O)_nA$ or $S(O)_nAr$, Ar' is naphthyl or phenyl which is unsubstituted or mono-, di- or trisubstituted by A, $OR^6$, $N(R^6)_2$, $NO_2$, CN, Hal, NHCOA, $COOR^6$, $CON(R^6)_2$, $COR^6$ or $S(O)_nA$, Hal is F, Cl, Br or I, n is 0, 1 or 2, or a salt thereof.

* * * * *